(12) United States Patent
MacMahon et al.

(10) Patent No.: US 11,033,544 B2
(45) Date of Patent: Jun. 15, 2021

(54) LOW-DOSE TRIPLE COMBINATION FORMULATION

(71) Applicant: THE GEORGE INSTITUTE FOR GLOBAL HEALTH, Sydney (AU)

(72) Inventors: Stephen MacMahon, Sydney (AU); Anthony Rodgers, Sydney (AU)

(73) Assignee: THE GEORGE INSTITUTE FOR GLOBAL HEALTH, Sydney (AU)

(*) Notice: Subject to any disclaimer, the term of this patent is extended or adjusted under 35 U.S.C. 154(b) by 0 days.

(21) Appl. No.: 16/364,063

(22) Filed: Mar. 25, 2019

(65) Prior Publication Data

US 2020/0306246 A1 Oct. 1, 2020

(51) Int. Cl.

| | | |
|---|---|---|
| *A61K 31/4985* | (2006.01) | |
| *A61K 31/155* | (2006.01) | |
| *A61P 3/10* | (2006.01) | |
| *A61K 31/351* | (2006.01) | |
| *A61K 31/7048* | (2006.01) | |
| *A61K 9/00* | (2006.01) | |
| *A61K 31/7034* | (2006.01) | |

(52) U.S. Cl.
CPC ........ *A61K 31/4985* (2013.01); *A61K 9/0053* (2013.01); *A61K 31/155* (2013.01); *A61K 31/351* (2013.01); *A61K 31/7034* (2013.01); *A61K 31/7048* (2013.01); *A61P 3/10* (2018.01)

(58) Field of Classification Search
None
See application file for complete search history.

(56) References Cited

U.S. PATENT DOCUMENTS

2016/0067217 A1* 3/2016 Kumar ................ A61K 31/415

FOREIGN PATENT DOCUMENTS

| WO | WO2008/116179 | * | 9/2008 | ............ A61K 31/70 |
| WO | WO2010/092125 | * | 8/2010 | ............ A61K 31/00 |
| WO | WO-2015173584 A1 | | 11/2015 | |

OTHER PUBLICATIONS

Ndefo et al., "Empagliflozin (Jardiance): A Novel SGLT2 Inhibitor for the Treatment of Type-2 Diabetes" P&T vol. 40 No. 6 pp. 364-368 (Year: 2015).*
FDA approved product information for Metformin single agent therapeutic composition, downloaded form accessdata.fda.gov (Year: 2019).*
FDA approved product information for dapagliflozin single agent therapeutic composition, downloaded form accessdata.fda.gov (Year: 2019).*
FDA approved product information for sitagliptin single agent therapeutic composition, downloaded form accessdata.fda.gov (Year: 2019).*
Package insert for SYNJARDY(R) oral tablets (empagliflozon/metformin hydrochloride, downloaded from accessdata.fda.gov (Year: 2017).*
Januvia(R) approval history, downloaded from https://www.drugs.com/history/januvia.html (Year: 2006).*

(Continued)

*Primary Examiner* — Eric Olson
(74) *Attorney, Agent, or Firm* — Wilson Sonsini Goodrich & Rosati

(57) ABSTRACT

Provided herein are pharmaceutical compositions that are useful for the treatment of diabetes and associated conditions, diseases, and disorders.

15 Claims, 3 Drawing Sheets

(56) References Cited

OTHER PUBLICATIONS

Farxiga(R) prescribing administration, downloaded from https://www.accessdata.fda.gov/drugsatfda_docs/label/2019/202293s015lbl.pdf (Year: 2014).*

Scott et al., "Efficacy and tolerability of the dipeptidyl peptidase-4 inhibitor sitagliptin as monotherapy over 12 weeks in patients with type 2 diabetes" International Journal of Clinical Practice vol. 61 issue 1 pp. 171-180 (Year: 2007).*

Ferrannini et al., "Dapagliflozin Monotherapy in Type 2 Diabetic Patients With Inadequate Glycemic Control by Diet and Exercise" Diabetes Care vol. 33 No. 10 pp. 2217-2224 (Year: 2010).*

Blonde et al., "Gastrointestinal tolerability of extended-release metformin tablets compared to immediate-release metformin tablets: results of a retrospective cohort study" Current Medical Research and Opinion vol. 20 No. 4 pp. 565-572 (Year: 2004).*

Amin et al. Two dose-ranging studies with PF -04937319, a systemic partial activator of glucokinase, as add-on therapy to metformin in adults with type 2 diabetes. Diabetes, Obesity and Metabolism 17:751-759 (2015).

Anderson et al. Dapagliflozin efficacy and safety: a perspective review. Ther Adv Drug Saf 5:242-254 (2014).

Arechavaleta et al. Efficacy and safety of treatment with sitagliptin or glimepiride in patients with type 2 diabetes inadequately controlled on metformin monotherapy: a randomized, double-blind, non-inferiority trial. Diabetes, Obesity, and Metabolism, 13:160-168 (Feb. 2011).

Bell. Combine and conquer: advantages and disadvantages of fixed-dose combination therapy. Diabetes Obes Metab 15(4):291-300 (2013).

Fuchigami et al. 21-LB: The study of dapagliflozin vs. sitagliptin treatment efficacy on prevention of cardiovascular risk factors in type 2 diabetes Patients: The DIVERSITYCVR Study. Diabetes: 68 (Supplement 1) (Jun. 2019).

Goldstein et al. Effect of initial combination therapy with sitagliptin, a dipeptidyl peptidase-4 inhibitor, and metformin on glycemic control in patients with type 2 diabetes. Diabetes Care 2007;30:1979-1987.

Jabbour et al. Dapagliflozin is effective as add-on therapy to sitagliptin with or without metformin: a 24-week, multicenter, randomized, double-blind, placebo- controlled study. Diabetes Care 37(3):740-750 (2014).

Kasichayanula et al. Lack of pharmacokinetic interaction between dapagliflozin, a novel sodium-glucose transporter 2 inhibitor, and metformin, pioglitazone, glimepiride or sitagliptin in healthy subjects. Diabetes, Obesity and Metabolism 3(1):47-54 (Nov. 2011).

Lavernia et al. Use of oral combination therapy for type 2 diabetes in primary care: Meeting individualized patient goals. Postgraduate Medicine 127(8):808-817 (2015).

Miller et al. Sitagliptin as combination therapy in the treatment of type 2 diabetes mellitus. Diabetes, Metabolic Syndrome and Obesity: Targets and Therapy 2:23-30 (2009).

Müller-Wieland et al. Efficacy and safety of dapagliflozin or dapagliflozin plus saxagliptin versus glimepiride as add-on to metformin in patients with type 2 diabetes. Diabetes Obesity and Metabolism 20:2598-2607 (2018).

PCT/IB2020/000214 International Search Report and Written Opinion dated May 11, 2020.

Urukazi et al. Glimepiride (0.5 mg/day) administration improves glycemic control without weight gain in Japanese type 2 diabetic patients. J Japan Diabetes Soc 50:835-841 (2007) (English Abstract).

* cited by examiner

LOW-DOSE TRIPLE COMBINATION FORMULATION

BACKGROUND

Diabetes mellitus (DM), commonly referred to as diabetes, is a group of metabolic disorders in which there are high blood sugar levels over a prolonged period. Symptoms of high blood sugar include frequent urination, increased thirst, and increased hunger. If left untreated, diabetes can cause many complications.

SUMMARY OF THE DISCLOSURE

In an aspect, provided herein is a pharmaceutical composition, comprising:
a) a dipeptidyl peptidase IV (DPP IV) inhibitor;
b) a biguanide; and
c) a subtype 2 sodium-glucose transport protein (SGLT2) inhibitor;
wherein (a), (b), and (c) are each at about 20% to about 75% of the lowest diabetes therapeutic dose (LDTD).

In an aspect, provided herein is a pharmaceutical composition consisting essentially of:
a) a DPP IV inhibitor;
b) a biguanide; and
c) a SGLT2 inhibitor;
wherein (a), (b), and (c) are each at about 20% to about 75% of the lowest diabetes therapeutic dose (LDTD).

In an aspect, provided herein is a pharmaceutical composition, comprising:
a) a dipeptidyl peptidase IV (DPP IV) inhibitor;
b) a biguanide; and
c) a subtype 2 sodium-glucose transport protein (SGLT2) inhibitor;
wherein (a) and (b) are each at about 65%-75% of the lowest diabetes therapeutic dose (LDTD), and (c) is at about 45%-55% of the lowest diabetes therapeutic dose (LDTD).

In an aspect, provided herein is a pharmaceutical composition consisting essentially of:
a) a DPP IV inhibitor;
b) a biguanide; and
c) a SGLT2 inhibitor;
wherein (a) and (b) are each at about 65%-75% of the lowest diabetes therapeutic dose (LDTD), and (c) is at about 45%-55% of the lowest diabetes therapeutic dose (LDTD).

In some embodiments, the DPP IV inhibitor is a gliptin. In some embodiments, the DPP IV inhibitor is selected from sitagliptin, vildagliptin, saxagliptin, linagliptin, gemigliptin, anagliptin, teneligliptin, alogliptin, trelagliptin, omarigliptin, evogliptin, gosogliptin, dutogliptin, or the pharmaceutically acceptable salt or hydrate thereof.

In some embodiments, the DPP IV inhibitor is sitagliptin or the pharmaceutically acceptable salt thereof. In some embodiments, the DPP IV inhibitor is sitagliptin phosphate.

In some embodiments, the biguanide is metformin or the pharmaceutically acceptable salt or hydrate thereof. In some embodiments, the biguanide is metformin hydrochloride.

In some embodiments, the metformin is formulated for immediate release. In some embodiments, the metformin is formulated for slow release.

In some embodiments, the SGLT2 inhibitor is a gliflozin. In some embodiments, the SGLT2 inhibitor is inhibitor is dapagliflozin, empagliflozin, canagliflozin, ipragliflozin (ASP-1941), tofogliflozin, remogliflozin, sergliflozin, ertugliflozin, sotagliflozin, or the pharmaceutically acceptable salt, hydrate, or combinations thereof. In some embodiments, the SGLT2 inhibitor is dapagliflozin or pharmaceutically acceptable salt, hydrate, or a combination thereof. In some embodiments, the SGLT2 inhibitor is empagliflozin or pharmaceutically acceptable salt, hydrate, or a combination thereof. In some embodiments, the SGLT2 inhibitor is a dapagliflozin hydrate. In some embodiments, the SGLT2 inhibitor is dapagliflozin propanediol monohydrate. In some embodiments, the SGLT2 inhibitor is dapagliflozin compounded with (2S)-1,2-propanediol, hydrate in a ratio of about 1:1:1.

In some embodiments, the dose of each (a), (b), and (c) is from about 40% to about 75% of the lowest diabetes therapeutic dose (LDTD).

In some embodiments, the dose of each (a), (b), and (c) is from about 60% to about 75% of the lowest diabetes therapeutic dose (LDTD). In some embodiments, the dose of each (a), (b), and (c) is from about 65% to about 75% of the lowest diabetes therapeutic dose (LDTD). In some embodiments, the dose of each (a), (b), and (c) is about 70% of the lowest diabetes therapeutic dose (LDTD).

In some embodiments, the dose of each (a), (b), and (c) is from about 40% to about 70% of the lowest diabetes therapeutic dose (LDTD).

In some embodiments, the dose of each (a), (b), and (c) is from about 40% to about 60% of the lowest diabetes therapeutic dose (LDTD). In some embodiments, the dose of each (a), (b), and (c) is from about 45% to about 55% of the lowest diabetes therapeutic dose (LDTD). In some embodiments, the dose of each (a), (b), and (c) is about 50% of the lowest diabetes therapeutic dose (LDTD).

In some embodiments, the DPP IV inhibitor is about 70% of the lowest diabetes therapeutic dose (LDTD) for the DPP IV inhibitor. In some embodiments, the DPP IV inhibitor is sitagliptin, and the dose of sitagliptin is about 17.5 mg.

In some embodiments, the DPP IV inhibitor is about 50% of the lowest diabetes therapeutic dose (LDTD) for the DPP IV inhibitor. In some embodiments, the DPP IV inhibitor is sitagliptin, and the dose of sitagliptin is about 12.5 mg.

In some embodiments, the biguanide is about 70% of the lowest diabetes therapeutic dose (LDTD) for the biguanide. In some embodiments, the biguanide is metformin hydrochloride, and the dose of metformin hydrochloride is about 350 mg.

In some embodiments, the biguanide is about 50% of the lowest diabetes therapeutic dose (LDTD) for the biguanide. In some embodiments, the biguanide is metformin hydrochloride, and the dose of metformin hydrochloride is about 250 mg.

In some embodiments, the SGLT2 inhibitor is about 50% of the lowest diabetes therapeutic dose (LDTD) for the SGLT2 inhibitor. In some embodiments, the SGLT2 inhibitor is dapagliflozin, and the dose of dapagliflozin is about 2.5 mg.

In some embodiments, the DPP IV inhibitor is sitagliptin, the biguanide is metformin, and the SGLT2 inhibitor is dapagliflozin.

In some embodiments, the dose of sitagliptin is from about 5.0 mg to about 18.75 mg, the dose of metformin is from about 100 mg to about 375 mg, and the dose of dapagliflozin is from about 1.0 mg to about 3.75 mg. In some embodiments, the dose of sitagliptin is from about 10 mg to about 16.25 mg, the dose of metformin is from about 200 mg to about 325 mg, and the dose of dapagliflozin is from about 2.0 mg to about 3.25 mg. In some embodiments, the dose of sitagliptin is from about 10 mg to about 15 mg, the dose of metformin is from about 200 mg to about 300 mg, and the dose of dapagliflozin is from about 2 mg to about 3 mg. In some embodiments, the dose of sitagliptin is from about 11.25 mg to about 13.75 mg, the dose of metformin is from about 225 mg to about 275 mg, and the dose of dapagliflozin is from about 2.25 mg to about 2.75 mg. In some embodiments, the dose of sitagliptin is about 12.5 mg, the dose of metformin is about 250 mg, and the dose of dapagliflozin is about 2.5 mg.

In some embodiments, the dose of each (a), (b), and (c) is from about 30% to about 40% of the lowest diabetes therapeutic dose (LDTD). In some embodiments, the dose of each (a), (b), and (c) is from about 30% to about 35% of the lowest diabetes therapeutic dose (LDTD). In some embodiments, the SGLT2 inhibitor is about 33% of the lowest diabetes therapeutic dose (LDTD) for the SGLT2 inhibitor.

In some embodiments, the SGLT2 inhibitor is dapagliflozin, and the dose of dapagliflozin is about 1.65 mg. In some embodiments, the SGLT2 inhibitor is empagliflozin, and the dose of empagliflozin is about 3.3 mg.

In some embodiments, the DPP IV inhibitor is sitagliptin, the biguanide is metformin, and the SGLT2 inhibitor is dapagliflozin or empagliflozin.

In some embodiments, the dose of sitagliptin is from about 7.5 mg to about 10 mg and the dose of metformin is from about 150 mg to about 200 mg. In some embodiments, the SGLT2 inhibitor is dapagliflozin and the dose of dapagliflozin is from about 1.5 mg to about 2.0 mg. In some embodiments, the SGLT2 inhibitor is empagliflozin and the dose of empagliflozin is from about 3.0 mg to about 4.0 mg. In some embodiments, the dose of sitagliptin is about 8.25 mg and the dose of metformin is about 165 mg. In some embodiments, the SGLT2 inhibitor is dapagliflozin and the dose of dapagliflozin is about 1.65 mg. In some embodiments, the SGLT2 inhibitor is empagliflozin, and the dose of empagliflozin is about 3.3 mg.

In some embodiments, the dose of each (a), (b), and (c) is from about 20% to about 30% of the lowest diabetes therapeutic dose (LDTD). In some embodiments, the dose of each (a), (b), and (c) is from about 22% to about 28% of the lowest diabetes therapeutic dose (LDTD). In some embodiments, the dose of the SGLT2 inhibitor is about 25% of the lowest diabetes therapeutic dose (LDTD) for the SGLT2 inhibitor.

In some embodiments, the SGLT2 inhibitor is dapagliflozin, and the dose of dapagliflozin is about 1.25 mg. In some embodiments, the SGLT2 inhibitor is empagliflozin, and the dose of empagliflozin is about 2.5 mg.

In some embodiments, the DPP IV inhibitor is sitagliptin, the biguanide is metformin, and the SGLT2 inhibitor is dapagliflozin or empagliflozin.

In some embodiments, the dose of sitagliptin is from about 5 mg to about 7.5 mg and the dose of metformin is from about 100 mg to about 150 mg.

In some embodiments, the SGLT2 inhibitor is dapagliflozin, and the dose of dapagliflozin is about 1.0 mg. In some embodiments, the SGLT2 inhibitor is empagliflozin, and the dose of empagliflozin is about 2.0 mg.

In some embodiments, the dose of sitagliptin is about 6.25 mg and the dose of metformin is about 150 mg.

In some embodiments, the SGLT2 inhibitor is dapagliflozin, and the dose of dapagliflozin is about 1.5 mg. In some embodiments, the SGLT2 inhibitor is empagliflozin, and the dose of empagliflozin is about 3.0 mg.

In some embodiments, the DPP IV inhibitor is sitagliptin and the dose of sitagliptin is from about 16.25 mg to about 18.75 mg.

In some embodiments, the biguanide is metformin and the dose of metformin is from about 325 mg to about 375 mg.

In some embodiments, the SGLT2 inhibitor is dapagliflozin, and the dose of dapagliflozin from about 2.25 mg to about 2.75 mg. In some embodiments, the SGLT2 inhibitor is empagliflozin, and the dose of empagliflozin from about 4.5 mg to about 7.5 mg.

In some embodiments, the DPP IV inhibitor is at about 70% of the lowest diabetes therapeutic dose (LDTD) for the DPP IV inhibitor.

In some embodiments, the biguanide is at about 70% of the lowest diabetes therapeutic dose (LDTD) for the biguanide.

In some embodiments, the SGLT2 inhibitor is at about 50% of the lowest diabetes therapeutic dose (LDTD) for the SGLT2 inhibitor.

In some embodiments, the DPP IV inhibitor is sitagliptin, the biguanide is metformin, and the SGLT2 inhibitor is dapagliflozin or empagliflozin.

In some embodiments, the dose of sitagliptin is about 17.5 mg, the dose of metformin is about 350 mg, and the dose of dapagliflozin is about 2.5 mg. In some embodiments, the dose of sitagliptin is about 17.5 mg, the dose of metformin is about 350 mg, and the dose of empagliflozin is about 5.0 mg.

In some embodiments, the DPP IV inhibitor is sitagliptin and the dose of the sitagliptin is about 17.5 mg.

In some embodiments, the biguanide is metformin and the dose of the metformin is about 350 mg.

In some embodiments, the SGLT2 inhibitor is dapagliflozin and the dose of the dapagliflozin is about 2.5 mg. In some embodiments, the SGLT2 inhibitor is empagliflozin and the dose of the empagliflozin is about 5.0 mg.

In some embodiments, a), (b), and (c) are provided in one formulation. In some embodiments, (a), (b), and (c) are each provided in a separate formulation. In some embodiments, two of the (a), (b), and (c) are provided in one formulation. In some embodiments, the pharmaceutical composition is in the form of pill, tablet or capsule. In some embodiments, the pharmaceutical composition is suitable for oral administration.

In another aspect, provided herein is a method of treating diabetes in a subject in need thereof, comprising administering any one of the pharmaceutical compositions disclosed herein.

In some embodiments, the treatment results in an improvement, slowing the progression of, or delaying a metabolic disorder such as diabetes mellitus, impaired glucose tolerance, impaired fasting blood glucose, hyperglycemia, postprandial hyperglycemia, overweight, obesity, metabolic syndrome, impaired renal function, gestational diabetes, new onset diabetes after transplantation (NODAT) and complications associated therewith, and post-transplant metabolic syndrome (PTMS) and complications associated therewith.

In some embodiments, the treatment results in an improvement, slowing the progression of, or delaying a metabolic disorder that is greater than that obtained with the full lowest diabetes therapeutic dose (LDTD) dose of any one of (a), (b), and (c) in the pharmaceutical composition. In some embodiments, the treatment results in greater long term tolerability and reduced risk of side effects when compared to treatment with the lowest diabetes therapeutic dose (LDTD) of any one of (a), (b), and (c) in the pharmaceutical composition. In some embodiments, the treatment is the initial or first-line treatment of diabetes. In some embodiments, the subject is not receiving any diabetes therapy prior to treatment. In some embodiments, the subject is receiving diabetes therapy prior to treatment and treatment with the formulations disclosed herein is second-line or maintenance treatment.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Figure 1:
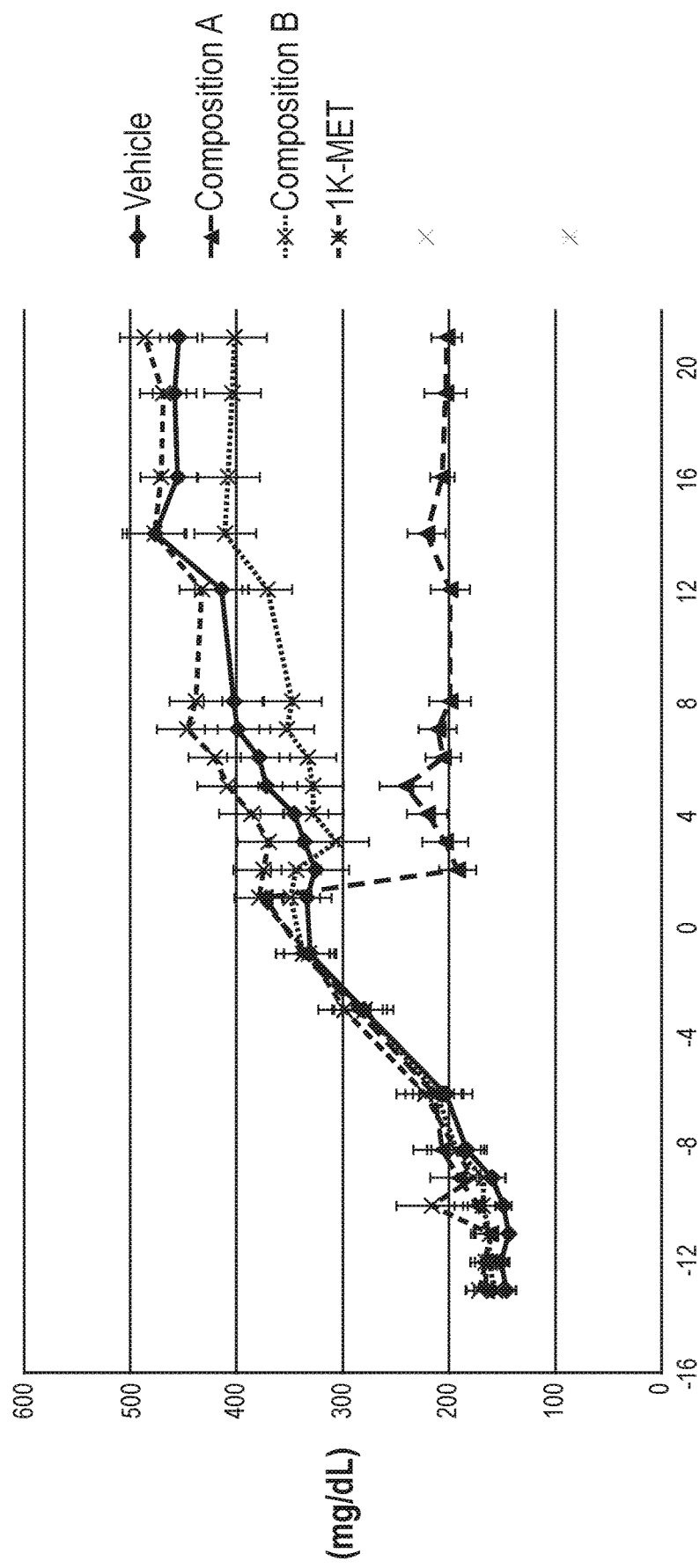
FIG. 1 shows non-fasting Whole blood glucose (mg/dL) post-dosing by treatment group.

Provided herein are pharmaceutical compositions for the treatment of diabetes comprising a DPP IV inhibitor, a biguanide, and an SGLT2 inhibitor. In some embodiments, the dose of each component is below the lowest dose approved for the treatment of diabetes. The present disclosure recognizes the technical effects of low-dose combination therapy set forth herein, including but not limited to, the use of low-doses to avoid or ameliorate side effects while retaining or improving benefits, the synergistic therapeutic benefits of certain drug combinations, the early introduction of combination therapy to improve therapeutic effects, etc. Described herein in one aspect are low-dose combination compositions for the treatment of diabetes, including the initial or first-line treatment of diabetes.

Certain Terminology

As used herein and in the appended claims, the singular forms "a," "and," and "the" include plural referents unless the context clearly dictates otherwise. Thus, for example, reference to "an agent" includes a plurality of such agents, and reference to "the composition" includes reference to one or more compositions (or to a plurality of compositions) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus in some embodiments, the number or numerical range varies between 1% and 10% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Pharmaceutically acceptable salt" as used herein includes both acid and base addition salts. In some embodiments, the pharmaceutically acceptable salt of any one of the compounds described herein is the form approved for use by the US Food and Drug Administration. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "hydrates" are compounds that contain either stoichiometric or non-stoichiometric amounts of water, and, in some embodiments, are formed during the process of crystallization with water. Hydrates are meant to include the hydrates of any one of the compounds described herein that is approved for use by the US Food and Drug Administration.

The term "acceptable" with respect to a formulation, composition or ingredient, as used herein, means having no persistent detrimental effect on the general health of the subject being treated.

The terms "administer," "administering," "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical, and rectal administration. Those of skill in the art are familiar with administration techniques that can be employed with the compounds and methods described herein. In some embodiments, the compounds and compositions described herein are administered orally.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refer to an approach for obtaining beneficial or desired results including but not limited to anti-diabetic effect, therapeutic benefit and/or a prophylactic benefit. By "therapeutic benefit" or "anti-diabetic effect" is meant eradication or amelioration of the underlying disorder being treated. A therapeutic benefit is achieved with the eradication or amelioration of one or more of the physiological symptoms associated with the underlying disorder (e.g., an improvement in: hyperglycemia, polyuria, polydipsia, polyphagia, diabetic dermadromes, etc.) such that an improvement is observed in the patient, notwithstanding that the patient may still be afflicted with the underlying disorder. Also, a therapeutic benefit is achieved with the eradication or amelioration of one or more of the complications associated with the underlying disorder (e.g., cardiovascular disease). For prophylactic benefit, the compositions may be administered to a patient at risk of developing a particular disease, or to a patient reporting one or more of the physiological symptoms of a disease, even though a diagnosis of this disease may not have been made.

The terms "diabetes" and "diabetes mellitus" are used interchangeably herein. These terms refers to type 1 diabetes mellitus, type 2 diabetes mellitus, complications of diabetes mellitus, and of neighboring disease states. As used herein, diabetes or diabetes mellitus (DM) refers to a group of metabolic disorders in which there are high blood sugar levels over a prolonged period.

Triple Compositions

Described herein are pharmaceutical compositions comprising: (a) a dipeptidyl peptidase IV (DPP IV) inhibitor; (b) a biguanide; and (c) a subtype 2 sodium-glucose transport protein (SGLT2) inhibitor;
wherein (a), (b), and (c) are each at about 20% to about 75% of the lowest diabetes therapeutic dose (LDTD).

Described herein are pharmaceutical compositions consisting essentially of: a) a dipeptidyl peptidase IV (DPP IV) inhibitor; b) a biguanide; and c) a subtype 2 sodium-glucose transport protein (SGLT2) inhibitor;
wherein (a), (b), and (c) are each at about 20% to about 75% of the lowest diabetes therapeutic dose (LDTD).

Described herein are pharmaceutical compositions comprising: a) a dipeptidyl peptidase IV (DPP IV) inhibitor; b) a biguanide; and c) a subtype 2 sodium-glucose transport protein (SGLT2) inhibitor;
wherein (a) and (b) are each at about 65%-75% of the lowest diabetes therapeutic dose (LDTD), and (c) is at about 45%-55% of the lowest diabetes therapeutic dose (LDTD).

Described herein are pharmaceutical compositions consisting essentially of: a) a DPP IV inhibitor; b) a biguanide; and c) a SGLT2 inhibitor;
wherein (a) and (b) are each at about 65%-75% of the lowest diabetes therapeutic dose (LDTD), and (c) is at about 45%-55% of the lowest diabetes therapeutic dose (LDTD).

In some embodiments, the DPP IV inhibitor is a gliptin. In some embodiments, the DPP IV inhibitor is selected from sitagliptin, vildagliptin, saxagliptin, linagliptin, gemigliptin, anagliptin, teneligliptin, alogliptin, trelagliptin, omarigliptin, evogliptin, gosogliptin, dutogliptin, or the pharmaceutically acceptable salt or hydrate thereof.

In some embodiments, the DPP IV inhibitor is sitagliptin or the pharmaceutically acceptable salt thereof. In some embodiments, the DPP IV inhibitor is sitagliptin phosphate.

In some embodiments, the biguanide is metformin or the pharmaceutically acceptable salt or hydrate thereof. In some embodiments, the biguanide is metformin hydrochloride.

In some embodiments, the metformin is formulated for immediate release. In some embodiments, the metformin is formulated for slow release.

In some embodiments, the SGLT2 inhibitor is a gliflozin. In some embodiments, the SGLT2 inhibitor is inhibitor is dapagliflozin, empagliflozin, canagliflozin, ipragliflozin (ASP-1941), tofogliflozin, remogliflozin, sergliflozin, ertugliflozin, sotagliflozin, or the pharmaceutically acceptable salt, hydrate, or combinations thereof. In some embodiments, the SGLT2 inhibitor is dapagliflozin or pharmaceutically acceptable salt, hydrate, or a combination thereof. In some embodiments, the SGLT2 inhibitor is empagliflozin or pharmaceutically acceptable salt, hydrate, or a combination thereof. In some embodiments, the SGLT2 inhibitor is a dapagliflozin hydrate. In some embodiments, the SGLT2 inhibitor is dapagliflozin propanediol monohydrate. In some embodiments, the SGLT2 inhibitor is dapagliflozin compounded with (2S)-1,2-propanediol, hydrate in a ratio of about 1:1:1.

In some embodiments, the dose of each (a), (b), and (c) is from about 40% to about 75% of the lowest diabetes therapeutic dose (LDTD).

In some embodiments, the dose of each (a), (b), and (c) is from about 60% to about 75% of the lowest diabetes therapeutic dose (LDTD). In some embodiments, the dose of each (a), (b), and (c) is from about 65% to about 75% of the lowest diabetes therapeutic dose (LDTD). In some embodiments, the dose of each (a), (b), and (c) is about 70% of the lowest diabetes therapeutic dose (LDTD).

In some embodiments, the dose of each (a), (b), and (c) is from about 40% to about 70% of the lowest diabetes therapeutic dose (LDTD).

In some embodiments, the dose of each (a), (b), and (c) is from about 40% to about 60% of the lowest diabetes therapeutic dose (LDTD). In some embodiments, the dose of each (a), (b), and (c) is from about 45% to about 55% of the lowest diabetes therapeutic dose (LDTD). In some embodiments, the dose of each (a), (b), and (c) is about 50% of the lowest diabetes therapeutic dose (LDTD).

In some embodiments, the DPP IV inhibitor is about 70% of the lowest diabetes therapeutic dose (LDTD) for the DPP IV inhibitor. In some embodiments, the DPP IV inhibitor is sitagliptin, and the dose of sitagliptin is about 17.5 mg.

In some embodiments, the DPP IV inhibitor is about 50% of the lowest diabetes therapeutic dose (LDTD) for the DPP IV inhibitor. In some embodiments, the DPP IV inhibitor is sitagliptin, and the dose of sitagliptin is about 12.5 mg.

In some embodiments, the biguanide is about 70% of the lowest diabetes therapeutic dose (LDTD) for the biguanide. In some embodiments, the biguanide is metformin hydrochloride, and the dose of metformin hydrochloride is about 350 mg.

In some embodiments, the biguanide is about 50% of the lowest diabetes therapeutic dose (LDTD) for the biguanide. In some embodiments, the biguanide is metformin hydrochloride, and the dose of metformin hydrochloride is about 250 mg.

In some embodiments, the SGLT2 inhibitor is about 50% of the lowest diabetes therapeutic dose (LDTD) for the SGLT2 inhibitor. In some embodiments, the SGLT2 inhibitor is dapagliflozin, and the dose of dapagliflozin is about 2.5 mg.

In some embodiments, the DPP IV inhibitor is sitagliptin, the biguanide is metformin, and the SGLT2 inhibitor is dapagliflozin.

In some embodiments, the dose of sitagliptin is from about 5.0 mg to about 18.75 mg, the dose of metformin is from about 100 mg to about 375 mg, and the dose of dapagliflozin is from about 1.0 mg to about 3.75 mg. In some embodiments, the dose of sitagliptin is from about 10 mg to about 16.25 mg, the dose of metformin is from about 200 mg to about 325 mg, and the dose of dapagliflozin is from about 2.0 mg to about 3.25 mg. In some embodiments, the dose of sitagliptin is from about 10 mg to about 15 mg, the dose of metformin is from about 200 mg to about 300 mg, and the dose of dapagliflozin is from about 2 mg to about 3 mg. In some embodiments, the dose of sitagliptin is from about 11.25 mg to about 13.75 mg, the dose of metformin is from about 225 mg to about 275 mg, and the dose of dapagliflozin is from about 2.25 mg to about 2.75 mg. In some embodiments, the dose of sitagliptin is about 12.5 mg, the dose of metformin is about 250 mg, and the dose of dapagliflozin is about 2.5 mg.

In some embodiments, the dose of each (a), (b), and (c) is from about 30% to about 40% of the lowest diabetes therapeutic dose (LDTD). In some embodiments, the dose of each (a), (b), and (c) is from about 30% to about 35% of the lowest diabetes therapeutic dose (LDTD). In some embodiments, the SGLT2 inhibitor is about 33% of the lowest diabetes therapeutic dose (LDTD) for the SGLT2 inhibitor.

In some embodiments, the SGLT2 inhibitor is dapagliflozin, and the dose of dapagliflozin is about 1.65 mg. In some embodiments, the SGLT2 inhibitor is empagliflozin, and the dose of empagliflozin is about 3.3 mg.

In some embodiments, the DPP IV inhibitor is sitagliptin, the biguanide is metformin, and the SGLT2 inhibitor is dapagliflozin or empagliflozin.

In some embodiments, the dose of sitagliptin is from about 7.5 mg to about 10 mg and the dose of metformin is from about 150 mg to about 200 mg. In some embodiments, the SGLT2 inhibitor is dapagliflozin and the dose of dapagliflozin is from about 1.5 mg to about 2.0 mg. In some embodiments, the SGLT2 inhibitor is empagliflozin and the dose of empagliflozin is from about 3.0 mg to about 4.0 mg. In some embodiments, the dose of sitagliptin is about 8.25 mg and the dose of metformin is about 165 mg. In some embodiments, the SGLT2 inhibitor is dapagliflozin and the dose of dapagliflozin is about 1.65 mg. In some embodiments, the SGLT2 inhibitor is empagliflozin, and the dose of empagliflozin is about 3.3 mg.

In some embodiments, the dose of each (a), (b), and (c) is from about 20% to about 30% of the lowest diabetes therapeutic dose (LDTD). In some embodiments, the dose of each (a), (b), and (c) is from about 22% to about 28% of the lowest diabetes therapeutic dose (LDTD). In some embodiments, the dose of the SGLT2 inhibitor is about 25% of the lowest diabetes therapeutic dose (LDTD) for the SGLT2 inhibitor.

In some embodiments, the SGLT2 inhibitor is dapagliflozin, and the dose of dapagliflozin is about 1.25 mg. In some embodiments, the SGLT2 inhibitor is empagliflozin, and the dose of empagliflozin is about 2.5 mg.

In some embodiments, the DPP IV inhibitor is sitagliptin, the biguanide is metformin, and the SGLT2 inhibitor is dapagliflozin or empagliflozin.

In some embodiments, the dose of sitagliptin is from about 5 mg to about 7.5 mg and the dose of metformin is from about 100 mg to about 150 mg.

In some embodiments, the SGLT2 inhibitor is dapagliflozin, and the dose of dapagliflozin is about 1.0 mg. In some embodiments, the SGLT2 inhibitor is empagliflozin, and the dose of empagliflozin is about 2.0 mg.

In some embodiments, the dose of sitagliptin is about 6.25 mg and the dose of metformin is about 150 mg.

In some embodiments, the SGLT2 inhibitor is dapagliflozin, and the dose of dapagliflozin is about 1.5 mg. In some embodiments, the SGLT2 inhibitor is empagliflozin, and the dose of empagliflozin is about 3.0 mg.

In some embodiments, the DPP IV inhibitor is sitagliptin and the dose of sitagliptin is from about 16.25 mg to about 18.75 mg.

In some embodiments, the biguanide is metformin and the dose of metformin is from about 325 mg to about 375 mg.

In some embodiments, the SGLT2 inhibitor is dapagliflozin, and the dose of dapagliflozin from about 2.25 mg to about 2.75 mg. In some embodiments, the SGLT2 inhibitor is empagliflozin, and the dose of empagliflozin from about 4.5 mg to about 7.5 mg.

In some embodiments, the DPP IV inhibitor is at about 70% of the lowest diabetes therapeutic dose (LDTD) for the DPP IV inhibitor.

In some embodiments, the biguanide is at about 70% of the lowest diabetes therapeutic dose (LDTD) for the biguanide.

In some embodiments, the SGLT2 inhibitor is at about 50% of the lowest diabetes therapeutic dose (LDTD) for the SGLT2 inhibitor.

In some embodiments, the DPP IV inhibitor is sitagliptin, the biguanide is metformin, and the SGLT2 inhibitor is dapagliflozin or empagliflozin.

In some embodiments, the dose of sitagliptin is about 17.5 mg, the dose of metformin is about 350 mg, and the dose of dapagliflozin is about 2.5 mg. In some embodiments, the dose of sitagliptin is about 17.5 mg, the dose of metformin is about 350 mg, and the dose of empagliflozin is about 5.0 mg.

In some embodiments, the DPP IV inhibitor is sitagliptin and the dose of the sitagliptin is about 17.5 mg.

In some embodiments, the biguanide is metformin and the dose of the metformin is about 350 mg.

In some embodiments, the SGLT2 inhibitor is dapagliflozin and the dose of the dapagliflozin is about 2.5 mg. In some embodiments, the SGLT2 inhibitor is empagliflozin and the dose of the empagliflozin is about 5.0 mg.

In some embodiments, a), (b), and (c) are provided in one formulation. In some embodiments, (a), (b), and (c) are each provided in a separate formulation. In some embodiments, two of the (a), (b), and (c) are provided in one formulation. In some embodiments, the pharmaceutical composition is in the form of pill, tablet or capsule. In some embodiments, the pharmaceutical composition is suitable for oral administration In some embodiments, the pharmaceutical compositions described herein comprise at least one pharmaceutically acceptable excipient. In some embodiments, the pharmaceutical compositions comprising (a) a DPP IV inhibitor; (b) a biguanide; and (c) an SGLT2 inhibitor described herein are essentially free of additional anti-hyperglycemic or anti-diabetic agents.

In some embodiments, the pharmaceutical composition comprises an anti-diabetic or anti-hyperglycemic combination of anti-diabetic active or anti-hyperglycemic agents, wherein the anti-diabetic or anti-hyperglycemic active agents consist of a DPP IV inhibitor; a biguanide; and an SGLT2 inhibitor.

In some embodiments, the pharmaceutical compositions disclosed herein achieve a significant anti-diabetic effect or therapeutic benefit in a subject with diabetes. In some embodiments, the pharmaceutical compositions disclosed herein achieve a significant anti-diabetic effect or therapeutic benefit in a subject with diabetes with minimum, insignificant, or no side effects.

DPP IV Inhibitors

As used herein, DPP IV inhibitors are compounds that block the enzyme dipeptidyl peptidase-4 (DPP IV) and reduce glucagon and blood glucose levels.

In some embodiments, the DPP IV inhibitor is a gliptin. In some embodiments, the DPP IV inhibitor is sitagliptin, vildagliptin, saxagliptin, linagliptin, gemigliptin, anagliptin, teneligliptin, alogliptin, trelagliptin, omarigliptin, evogliptin, gosogliptin, dutogliptin, or the pharmaceutically acceptable salt or hydrate thereof.

In some embodiments, the DPP IV inhibitor is sitagliptin, or the pharmaceutically acceptable salt or hydrate thereof. In some embodiments, the DPP IV inhibitor is sitagliptin phosphate, or a hydrate thereof. In some embodiments, the DPP IV inhibitor is vildagliptin, or the pharmaceutically acceptable salt or hydrate thereof. In some embodiments, the DPP IV inhibitor is saxagliptin, or the pharmaceutically acceptable salt or hydrate thereof. In some embodiments, the DPP IV inhibitor is linagliptin, or the pharmaceutically acceptable salt or hydrate thereof. In some embodiments, the DPP IV inhibitor is gemigliptin, or the pharmaceutically acceptable salt or hydrate thereof. In some embodiments, the DPP IV inhibitor is anagliptin, or the pharmaceutically acceptable salt or hydrate thereof. In some embodiments, the DPP IV inhibitor is teneligliptin, or the pharmaceutically acceptable salt or hydrate thereof. In some embodiments, the DPP IV inhibitor is alogliptin. In some embodiments, the DPP IV inhibitor is trelagliptin, or the pharmaceutically acceptable salt or hydrate thereof. In some embodiments, the DPP IV inhibitor is omarigliptin, or the pharmaceutically acceptable salt or hydrate thereof. In some embodiments, the DPP IV inhibitor is evogliptin, or the pharmaceutically acceptable salt or hydrate thereof. In some embodiments, the DPP IV inhibitor is gosogliptin, or the pharmaceutically acceptable salt or hydrate thereof. In some embodiments, the DPP IV inhibitor is dutogliptin, or the pharmaceutically acceptable salt or hydrate thereof.

Biguanides

As used herein, biguanides are compounds that refer to a class of drugs that function as oral antihyperglycemic drugs used for diabetes mellitus or prediabetes treatment.

In some embodiments, the biguanide is metformin. In some embodiments, the biguanide is metformin hydrochloride, or a hydrate thereof.

SGLT2 Inhibitors

As used herein, SGLT2 inhibitors are compounds that lead to a reduction in blood glucose levels.

In some embodiments, the is selected from dapagliflozin, empagliflozin, canagliflozin, ipragliflozin (ASP-1941), tofogliflozin, remogliflozin, sergliflozin, ertugliflozin, sotagliflozin, or the pharmaceutically acceptable salt or hydrate thereof. In some embodiments, the SGLT2 inhibitor is dapagflozin, or the pharmaceutically acceptable salt or hydrate thereof. In some embodiments, the SGLT2 inhibitor is empagflozin, or the pharmaceutically acceptable salt or hydrate thereof. In some embodiments, the SGLT2 inhibitor is canagliflozin, or the pharmaceutically acceptable salt or hydrate thereof. In some embodiments, the SGLT2 inhibitor is ipragliflozin (ASP-1941), or the pharmaceutically acceptable salt or hydrate thereof. In some embodiments, the SGLT2 inhibitor is tofogliflozin, or the pharmaceutically acceptable salt or hydrate thereof. In some embodiments, the SGLT2 inhibitor is remogliflozin, or the pharmaceutically acceptable salt or hydrate thereof. In some embodiments, the SGLT2 inhibitor is sergliflozin, or the pharmaceutically acceptable salt or hydrate thereof. In some embodiments, the SGLT2 inhibitor is ertugliflozin, or the pharmaceutically acceptable salt or hydrate thereof. In some embodiments, the SGLT2 inhibitor is sotagliflozin, or the pharmaceutically acceptable salt or hydrate thereof.

Lowest Diabetes Therapeutic Dose

As used herein, the lowest diabetes therapeutic dose (LDTD) refers to the lowest strength dose for the single agent for diabetes approved by the US Food and Drug Administration and is not marked as "discontinued" by the Orange Book database (world-wide web at address accessdata.fda.gov/scripts/cder/ob/) as of the filing date of this application. The lowest diabetes therapeutic dose does not include the lowest manufactured dose for cases wherein the lowest diabetes therapeutic dose is not the same as the lowest manufactured dose. Furthermore, the lowest diabetes therapeutic dose does not include the dose as recommended by a physician for cases wherein the lowest diabetes therapeutic dose is not the same dose as recommended by a physician. Further, the lowest diabetes dose of the DPP IV inhibitors, biguanides, and SGLT2 inhibitors, described herein refers to the dose of the form of DPP IV inhibitors, biguanides, and SGLT2 inhibitors approved for use by the US Food and Drug Administration, which includes the free base, pharmaceutically acceptable salt, or hydrate thereof.

In some embodiments, the dose of the DPP IV inhibitor is from about 20% to about 75% of the lowest diabetes therapeutic dose. In some embodiments, the dose of the DPP IV inhibitor is from about 20% to about 70% of the lowest diabetes therapeutic dose. In some embodiments, the dose of the DPP IV inhibitor is from about 20% to about 65% of the lowest diabetes therapeutic dose. In some embodiments, the dose of the DPP IV inhibitor is from about 20% to about 60% of the lowest diabetes therapeutic dose. In some embodiments, the dose of the DPP IV inhibitor is from about 20% to about 55% of the lowest diabetes therapeutic dose. In some embodiments, the dose of the DPP IV inhibitor is from about 20% to about 50% of the lowest diabetes therapeutic dose. In some embodiments, the dose of the DPP IV inhibitor is from about 20% to about 45% of the lowest diabetes therapeutic dose. In some embodiments, the dose of the DPP IV inhibitor is from about 20% to about 40% of the lowest diabetes therapeutic dose. In some embodiments, the dose of the DPP IV inhibitor is from about 20% to about 35% of the lowest diabetes therapeutic dose. In some embodiments, the dose of the DPP IV inhibitor is from about 20% to about 30% of the lowest diabetes therapeutic dose. In some embodiments, the dose of the DPP IV inhibitor is from about 20% to about 25% of the lowest diabetes therapeutic dose.

In some embodiments, the dose of the DPP IV inhibitor is from about 25% to about 75% of the lowest diabetes therapeutic dose. In some embodiments, the dose of the DPP IV inhibitor is from about 25% to about 70% of the lowest diabetes therapeutic dose. In some embodiments, the dose of the DPP IV inhibitor is from about 25% to about 65% of the lowest diabetes therapeutic dose. In some embodiments, the dose of the DPP IV inhibitor is from about 25% to about 60% of the lowest diabetes therapeutic dose. In some embodiments, the dose of the DPP IV inhibitor is from about 25% to about 55% of the lowest diabetes therapeutic dose. In some embodiments, the dose of the DPP IV inhibitor is from about 25% to about 50% of the lowest diabetes therapeutic dose. In some embodiments, the dose of the DPP IV inhibitor is from about 25% to about 45% of the lowest diabetes therapeutic dose. In some embodiments, the dose of the DPP IV inhibitor is from about 25% to about 40% of the lowest diabetes therapeutic dose. In some embodiments, the dose of the DPP IV inhibitor is from about 25% to about 35% of the lowest diabetes therapeutic dose. In some embodiments, the dose of the DPP IV inhibitor is from about 25% to about 30% of the lowest diabetes therapeutic dose.

In some embodiments, the dose of the DPP IV inhibitor is from about 30% to about 75% of the lowest diabetes therapeutic dose. In some embodiments, the dose of the DPP IV inhibitor is from about 30% to about 70% of the lowest diabetes therapeutic dose. In some embodiments, the dose of the DPP IV inhibitor is from about 30% to about 65% of the lowest diabetes therapeutic dose. In some embodiments, the dose of the DPP IV inhibitor is from about 30% to about 60% of the lowest diabetes therapeutic dose. In some embodiments, the dose of the DPP IV inhibitor is from about 30% to about 55% of the lowest diabetes therapeutic dose. In some embodiments, the dose of the DPP IV inhibitor is from about 30% to about 50% of the lowest diabetes therapeutic dose. In some embodiments, the dose of the DPP IV inhibitor is from about 30% to about 45% of the lowest diabetes therapeutic dose. In some embodiments, the dose of the DPP IV inhibitor is from about 30% to about 40% of the lowest diabetes therapeutic dose. In some embodiments, the dose of the DPP IV inhibitor is from about 30% to about 35% of the lowest diabetes therapeutic dose.

In some embodiments, the dose of the DPP IV inhibitor is from about 35% to about 75% of the lowest diabetes therapeutic dose. In some embodiments, the dose of the DPP IV inhibitor is from about 35% to about 70% of the lowest diabetes therapeutic dose. In some embodiments, the dose of the DPP IV inhibitor is from about 35% to about 65% of the lowest diabetes therapeutic dose. In some embodiments, the dose of the DPP IV inhibitor is from about 35% to about 60% of the lowest diabetes therapeutic dose. In some embodiments, the dose of the DPP IV inhibitor is from about 35% to about 55% of the lowest diabetes therapeutic dose. In some embodiments, the dose of the DPP IV inhibitor is from about 35% to about 50% of the lowest diabetes therapeutic dose. In some embodiments, the dose of the DPP IV inhibitor is from about 35% to about 45% of the lowest diabetes therapeutic dose. In some embodiments, the dose of the DPP IV inhibitor is from about 35% to about 40% of the lowest diabetes therapeutic dose In some embodiments, the dose of the DPP IV inhibitor is from about 40% to about 75% of the lowest diabetes therapeutic dose. In some embodiments, the dose of the DPP IV inhibitor is from about 40% to about 70% of the lowest diabetes therapeutic dose. In some embodiments, the dose of the DPP IV inhibitor is from about 40% to about 65% of the lowest diabetes therapeutic dose. In some embodiments, the dose of the DPP IV inhibitor is from about 40% to about 60% of the lowest diabetes therapeutic dose. In some embodiments, the dose of the DPP IV inhibitor is from about 40% to about 55% of the lowest diabetes therapeutic dose. In some embodiments, the dose of the DPP IV inhibitor is from about 40% to about 50% of the lowest diabetes therapeutic dose. In some embodiments, the dose of the DPP IV inhibitor is from about 40% to about 45% of the lowest diabetes therapeutic dose.

In some embodiments, the dose of the DPP IV inhibitor is from about 45% to about 75% of the lowest diabetes therapeutic dose. In some embodiments, the dose of the DPP IV inhibitor is from about 45% to about 70% of the lowest diabetes therapeutic dose. In some embodiments, the dose of the DPP IV inhibitor is from about 45% to about 65% of the lowest diabetes therapeutic dose. In some embodiments, the dose of the DPP IV inhibitor is from about 45% to about 60% of the lowest diabetes therapeutic dose. In some embodiments, the dose of the DPP IV inhibitor is from about 45% to about 55% of the lowest diabetes therapeutic dose. In some embodiments, the dose of the DPP IV inhibitor is from about 45% to about 50% of the lowest diabetes therapeutic dose.

In some embodiments, the dose of the DPP IV inhibitor is from about 50% to about 75% of the lowest diabetes therapeutic dose. In some embodiments, the dose of the DPP IV inhibitor is from about 50% to about 70% of the lowest diabetes therapeutic dose. In some embodiments, the dose of the DPP IV inhibitor is from about 50% to about 65% of the lowest diabetes therapeutic dose. In some embodiments, the dose of the DPP IV inhibitor is from about 50% to about 60% of the lowest diabetes therapeutic dose. In some embodiments, the dose of the DPP IV inhibitor is from about 50% to about 55% of the lowest diabetes therapeutic dose.

In some embodiments, the dose of the DPP IV inhibitor is from about 55% to about 75% of the lowest diabetes therapeutic dose. In some embodiments, the dose of the DPP IV inhibitor is from about 55% to about 70% of the lowest diabetes therapeutic dose. In some embodiments, the dose of the DPP IV inhibitor is from about 55% to about 65% of the lowest diabetes therapeutic dose. In some embodiments, the dose of the DPP IV inhibitor is from about 55% to about 60% of the lowest diabetes therapeutic dose.

In some embodiments, the dose of the DPP IV inhibitor is from about 60% to about 75% of the lowest diabetes therapeutic dose. In some embodiments, the dose of the DPP IV inhibitor is from about 60% to about 70% of the lowest diabetes therapeutic dose. In some embodiments, the dose of the DPP IV inhibitor is from about 60% to about 65% of the lowest diabetes therapeutic dose.

In some embodiments, the dose of the DPP IV inhibitor is from about 65% to about 75% of the lowest diabetes therapeutic dose. In some embodiments, the dose of the DPP IV inhibitor is from about 65% to about 70% of the lowest diabetes therapeutic dose.

In some embodiments, the dose of the DPP IV inhibitor is from about 70% to about 75% of the lowest diabetes therapeutic dose.

In some embodiments, the dose of the biguanide is from about 20% to about 75% of the lowest diabetes therapeutic dose. In some embodiments, the dose of the biguanide is from about 20% to about 70% of the lowest diabetes therapeutic dose. In some embodiments, the dose of the biguanide is from about 20% to about 65% of the lowest diabetes therapeutic dose. In some embodiments, the dose of the biguanide is from about 20% to about 60% of the lowest diabetes therapeutic dose. In some embodiments, the dose of the biguanide is from about 20% to about 55% of the lowest diabetes therapeutic dose. In some embodiments, the dose of the biguanide is from about 20% to about 50% of the lowest diabetes therapeutic dose. In some embodiments, the dose of the biguanide is from about 20% to about 45% of the lowest diabetes therapeutic dose. In some embodiments, the dose of the biguanide is from about 20% to about 40% of the lowest diabetes therapeutic dose. In some embodiments, the dose of the biguanide is from about 20% to about 35% of the lowest diabetes therapeutic dose. In some embodiments, the dose of the biguanide is from about 20% to about 30% of the lowest diabetes therapeutic dose. In some embodiments, the dose of the biguanide is from about 20% to about 25% of the lowest diabetes therapeutic dose.

In some embodiments, the dose of the biguanide is from about 25% to about 75% of the lowest diabetes therapeutic dose. In some embodiments, the dose of the biguanide is from about 25% to about 70% of the lowest diabetes therapeutic dose. In some embodiments, the dose of the biguanide is from about 25% to about 65% of the lowest diabetes therapeutic dose. In some embodiments, the dose of the biguanide is from about 25% to about 60% of the lowest diabetes therapeutic dose. In some embodiments, the dose of the biguanide is from about 25% to about 55% of the lowest diabetes therapeutic dose. In some embodiments, the dose of the biguanide is from about 25% to about 50% of the lowest diabetes therapeutic dose. In some embodiments, the dose of the biguanide is from about 25% to about 45% of the lowest diabetes therapeutic dose. In some embodiments, the dose of the biguanide is from about 25% to about 40% of the lowest diabetes therapeutic dose. In some embodiments, the dose of the biguanide is from about 25% to about 35% of the lowest diabetes therapeutic dose. In some embodiments, the dose of the biguanide is from about 25% to about 30% of the lowest diabetes therapeutic dose.

In some embodiments, the dose of the biguanide is from about 30% to about 75% of the lowest diabetes therapeutic dose. In some embodiments, the dose of the biguanide is from about 30% to about 70% of the lowest diabetes therapeutic dose. In some embodiments, the dose of the biguanide is from about 30% to about 65% of the lowest diabetes therapeutic dose. In some embodiments, the dose of the biguanide is from about 30% to about 60% of the lowest diabetes therapeutic dose. In some embodiments, the dose of the biguanide is from about 30% to about 55% of the lowest diabetes therapeutic dose. In some embodiments, the dose of the biguanide is from about 30% to about 50% of the lowest diabetes therapeutic dose. In some embodiments, the dose of the biguanide is from about 30% to about 45% of the lowest diabetes therapeutic dose. In some embodiments, the dose of the biguanide is from about 30% to about 40% of the lowest diabetes therapeutic dose. In some embodiments, the dose of the biguanide is from about 30% to about 35% of the lowest diabetes therapeutic dose.

In some embodiments, the dose of the biguanide is from about 35% to about 75% of the lowest diabetes therapeutic dose. In some embodiments, the dose of the biguanide is from about 35% to about 70% of the lowest diabetes therapeutic dose. In some embodiments, the dose of the biguanide is from about 35% to about 65% of the lowest diabetes therapeutic dose. In some embodiments, the dose of the biguanide is from about 35% to about 60% of the lowest diabetes therapeutic dose. In some embodiments, the dose of the biguanide is from about 35% to about 55% of the lowest diabetes therapeutic dose. In some embodiments, the dose of the biguanide is from about 35% to about 50% of the lowest diabetes therapeutic dose. In some embodiments, the dose of the biguanide is from about 35% to about 45% of the lowest diabetes therapeutic dose. In some embodiments, the dose of the biguanide is from about 35% to about 40% of the lowest diabetes therapeutic dose In some embodiments, the dose of the biguanide is from about 40% to about 75% of the lowest diabetes therapeutic dose. In some embodiments, the dose of the biguanide is from about 40% to about 70% of the lowest diabetes therapeutic dose. In some embodiments, the dose of the biguanide is from about 40% to about 65% of the lowest diabetes therapeutic dose. In some embodiments, the dose of the biguanide is from about 40% to about 60% of the lowest diabetes therapeutic dose. In some embodiments, the dose of the biguanide is from about 40% to about 55% of the lowest diabetes therapeutic dose. In some embodiments, the dose of the biguanide is from about 40% to about 50% of the lowest diabetes therapeutic dose. In some embodiments, the dose of the biguanide is from about 40% to about 45% of the lowest diabetes therapeutic dose.

In some embodiments, the dose of the biguanide is from about 45% to about 75% of the lowest diabetes therapeutic dose. In some embodiments, the dose of the biguanide is from about 45% to about 70% of the lowest diabetes therapeutic dose. In some embodiments, the dose of the biguanide is from about 45% to about 65% of the lowest diabetes therapeutic dose. In some embodiments, the dose of the biguanide is from about 45% to about 60% of the lowest diabetes therapeutic dose. In some embodiments, the dose of the biguanide is from about 45% to about 55% of the lowest diabetes therapeutic dose. In some embodiments, the dose of the biguanide is from about 45% to about 50% of the lowest diabetes therapeutic dose.

In some embodiments, the dose of the biguanide is from about 50% to about 75% of the lowest diabetes therapeutic dose. In some embodiments, the dose of the biguanide is from about 50% to about 70% of the lowest diabetes therapeutic dose. In some embodiments, the dose of the biguanide is from about 50% to about 65% of the lowest diabetes therapeutic dose. In some embodiments, the dose of the biguanide is from about 50% to about 60% of the lowest diabetes therapeutic dose. In some embodiments, the dose of the biguanide is from about 50% to about 55% of the lowest diabetes therapeutic dose.

In some embodiments, the dose of the biguanide is from about 55% to about 75% of the lowest diabetes therapeutic dose. In some embodiments, the dose of the biguanide is from about 55% to about 70% of the lowest diabetes therapeutic dose. In some embodiments, the dose of the biguanide is from about 55% to about 65% of the lowest diabetes therapeutic dose. In some embodiments, the dose of the biguanide is from about 55% to about 60% of the lowest diabetes therapeutic dose.

In some embodiments, the dose of the biguanide is from about 60% to about 75% of the lowest diabetes therapeutic dose. In some embodiments, the dose of the biguanide is from about 60% to about 70% of the lowest diabetes therapeutic dose. In some embodiments, the dose of the biguanide is from about 60% to about 65% of the lowest diabetes therapeutic dose.

In some embodiments, the dose of the biguanide is from about 65% to about 75% of the lowest diabetes therapeutic dose. In some embodiments, the dose of the biguanide is from about 65% to about 70% of the lowest diabetes therapeutic dose.

In some embodiments, the dose of the biguanide is from about 70% to about 75% of the lowest diabetes therapeutic dose.

In some embodiments, the dose of the SGLT2 inhibitor is from about 20% to about 75% of the lowest diabetes therapeutic dose. In some embodiments, the dose of the SGLT2 inhibitor is from about 20% to about 70% of the lowest diabetes therapeutic dose. In some embodiments, the dose of the SGLT2 inhibitor is from about 20% to about 65% of the lowest diabetes therapeutic dose. In some embodiments, the dose of the SGLT2 inhibitor is from about 20% to about 60% of the lowest diabetes therapeutic dose. In some embodiments, the dose of the SGLT2 inhibitor is from about 20% to about 55% of the lowest diabetes therapeutic dose. In some embodiments, the dose of the SGLT2 inhibitor is from about 20% to about 50% of the lowest diabetes therapeutic dose. In some embodiments, the dose of the SGLT2 inhibitor is from about 20% to about 45% of the lowest diabetes therapeutic dose. In some embodiments, the dose of the SGLT2 inhibitor is from about 20% to about 40% of the lowest diabetes therapeutic dose. In some embodiments, the dose of the SGLT2 inhibitor is from about 20% to about 35% of the lowest diabetes therapeutic dose. In some embodiments, the dose of the SGLT2 inhibitor is from about 20% to about 30% of the lowest diabetes therapeutic dose. In some embodiments, the dose of the SGLT2 inhibitor is from about 20% to about 25% of the lowest diabetes therapeutic dose.

In some embodiments, the dose of the SGLT2 inhibitor is from about 25% to about 75% of the lowest diabetes therapeutic dose. In some embodiments, the dose of the SGLT2 inhibitor is from about 25% to about 70% of the lowest diabetes therapeutic dose. In some embodiments, the dose of the SGLT2 inhibitor is from about 25% to about 65% of the lowest diabetes therapeutic dose. In some embodiments, the dose of the SGLT2 inhibitor is from about 25% to about 60% of the lowest diabetes therapeutic dose. In some embodiments, the dose of the SGLT2 inhibitor is from about 25% to about 55% of the lowest diabetes therapeutic dose. In some embodiments, the dose of the SGLT2 inhibitor is from about 25% to about 50% of the lowest diabetes therapeutic dose. In some embodiments, the dose of the SGLT2 inhibitor is from about 25% to about 45% of the lowest diabetes therapeutic dose. In some embodiments, the dose of the SGLT2 inhibitor is from about 25% to about 40% of the lowest diabetes therapeutic dose. In some embodiments, the dose of the SGLT2 inhibitor is from about 25% to about 35% of the lowest diabetes therapeutic dose. In some embodiments, the dose of the SGLT2 inhibitor is from about 25% to about 30% of the lowest diabetes therapeutic dose.

In some embodiments, the dose of the SGLT2 inhibitor is from about 30% to about 75% of the lowest diabetes therapeutic dose. In some embodiments, the dose of the SGLT2 inhibitor is from about 30% to about 70% of the lowest diabetes therapeutic dose. In some embodiments, the dose of the SGLT2 inhibitor is from about 30% to about 65% of the lowest diabetes therapeutic dose. In some embodiments, the dose of the SGLT2 inhibitor is from about 30% to about 60% of the lowest diabetes therapeutic dose. In some embodiments, the dose of the SGLT2 inhibitor is from about 30% to about 55% of the lowest diabetes therapeutic dose. In some embodiments, the dose of the SGLT2 inhibitor is from about 30% to about 50% of the lowest diabetes therapeutic dose. In some embodiments, the dose of the SGLT2 inhibitor is from about 30% to about 45% of the lowest diabetes therapeutic dose. In some embodiments, the dose of the SGLT2 inhibitor is from about 30% to about 40% of the lowest diabetes therapeutic dose. In some embodiments, the dose of the SGLT2 inhibitor is from about 30% to about 35% of the lowest diabetes therapeutic dose.

In some embodiments, the dose of the SGLT2 inhibitor is from about 35% to about 75% of the lowest diabetes therapeutic dose. In some embodiments, the dose of the SGLT2 inhibitor is from about 35% to about 70% of the lowest diabetes therapeutic dose. In some embodiments, the dose of the SGLT2 inhibitor is from about 35% to about 65% of the lowest diabetes therapeutic dose. In some embodiments, the dose of the SGLT2 inhibitor is from about 35% to about 60% of the lowest diabetes therapeutic dose. In some embodiments, the dose of the SGLT2 inhibitor is from about 35% to about 55% of the lowest diabetes therapeutic dose. In some embodiments, the dose of the SGLT2 inhibitor is from about 35% to about 50% of the lowest diabetes therapeutic dose. In some embodiments, the dose of the SGLT2 inhibitor is from about 35% to about 45% of the lowest diabetes therapeutic dose. In some embodiments, the dose of the SGLT2 inhibitor is from about 35% to about 40% of the lowest diabetes therapeutic dose In some embodiments, the dose of the SGLT2 inhibitor is from about 40% to about 75% of the lowest diabetes therapeutic dose. In some embodiments, the dose of the SGLT2 inhibitor is from about 40% to about 70% of the lowest diabetes therapeutic dose. In some embodiments, the dose of the SGLT2 inhibitor is from about 40% to about 65% of the lowest diabetes therapeutic dose. In some embodiments, the dose of the SGLT2 inhibitor is from about 40% to about 60% of the lowest diabetes therapeutic dose. In some embodiments, the dose of the SGLT2 inhibitor is from about 40% to about 55% of the lowest diabetes therapeutic dose. In some embodiments, the dose of the SGLT2 inhibitor is from about 40% to about 50% of the lowest diabetes therapeutic dose. In some embodiments, the dose of the SGLT2 inhibitor is from about 40% to about 45% of the lowest diabetes therapeutic dose.

In some embodiments, the dose of the SGLT2 inhibitor is from about 45% to about 75% of the lowest diabetes therapeutic dose. In some embodiments, the dose of the SGLT2 inhibitor is from about 45% to about 70% of the lowest diabetes therapeutic dose. In some embodiments, the dose of the SGLT2 inhibitor is from about 45% to about 65% of the lowest diabetes therapeutic dose. In some embodiments, the dose of the SGLT2 inhibitor is from about 45% to about 60% of the lowest diabetes therapeutic dose. In some embodiments, the dose of the SGLT2 inhibitor is from about 45% to about 55% of the lowest diabetes therapeutic dose. In some embodiments, the dose of the SGLT2 inhibitor is from about 45% to about 50% of the lowest diabetes therapeutic dose.

In some embodiments, the dose of the SGLT2 inhibitor is from about 50% to about 75% of the lowest diabetes therapeutic dose. In some embodiments, the dose of the SGLT2 inhibitor is from about 50% to about 70% of the lowest diabetes therapeutic dose. In some embodiments, the dose of the SGLT2 inhibitor is from about 50% to about 65% of the lowest diabetes therapeutic dose. In some embodiments, the dose of the SGLT2 inhibitor is from about 50% to about 60% of the lowest diabetes therapeutic dose. In some embodiments, the dose of the SGLT2 inhibitor is from about 50% to about 55% of the lowest diabetes therapeutic dose.

In some embodiments, the dose of the SGLT2 inhibitor is from about 55% to about 75% of the lowest diabetes therapeutic dose. In some embodiments, the dose of the SGLT2 inhibitor is from about 55% to about 70% of the lowest diabetes therapeutic dose. In some embodiments, the dose of the SGLT2 inhibitor is from about 55% to about 65% of the lowest diabetes therapeutic dose. In some embodiments, the dose of the SGLT2 inhibitor is from about 55% to about 60% of the lowest diabetes therapeutic dose.

In some embodiments, the dose of the SGLT2 inhibitor is from about 60% to about 75% of the lowest diabetes therapeutic dose. In some embodiments, the dose of the SGLT2 inhibitor is from about 60% to about 70% of the lowest diabetes therapeutic dose. In some embodiments, the dose of the SGLT2 inhibitor is from about 60% to about 65% of the lowest diabetes therapeutic dose.

In some embodiments, the dose of the SGLT2 inhibitor is from about 65% to about 75% of the lowest diabetes therapeutic dose. In some embodiments, the dose of the SGLT2 inhibitor is from about 65% to about 70% of the lowest diabetes therapeutic dose.

In some embodiments, the dose of the SGLT2 inhibitor is from about 70% to about 75% of the lowest diabetes therapeutic dose.

In some embodiments, the dose of the DPP IV inhibitor is from about 20% to about 50% of the lowest diabetes therapeutic dose. In some embodiments, the dose of the DPP IV inhibitor is from about 20% to about 45% of the lowest diabetes therapeutic dose. In some embodiments, the dose of the DPP IV inhibitor is from about 20% to about 40% of the lowest diabetes therapeutic dose. In some embodiments, the dose of the DPP IV inhibitor is from about 20% to about 35% of the lowest diabetes therapeutic dose. In some embodiments, the dose of the DPP IV inhibitor is from about 20% to about 30% of the lowest diabetes therapeutic dose. In some embodiments, the dose of the DPP IV inhibitor is from about 20% to about 25% of the lowest diabetes therapeutic dose.

In some embodiments, the dose of the DPP IV inhibitor is from about 25% to about 50% of the lowest diabetes therapeutic dose. In some embodiments, the dose of the DPP IV inhibitor is from about 25% to about 45% of the lowest diabetes therapeutic dose. In some embodiments, the dose of the DPP IV inhibitor is from about 25% to about 40% of the lowest diabetes therapeutic dose. In some embodiments, the dose of the DPP IV inhibitor is from about 25% to about 35% of the lowest diabetes therapeutic dose. In some embodiments, the dose of the DPP IV inhibitor is from about 25% to about 30% of the lowest diabetes therapeutic dose.

In some embodiments, the dose of the DPP IV inhibitor is from about 30% to about 50% of the lowest diabetes therapeutic dose. In some embodiments, the dose of the DPP IV inhibitor is from about 30% to about 45% of the lowest diabetes therapeutic dose. In some embodiments, the dose of the DPP IV inhibitor is from about 30% to about 40% of the lowest diabetes therapeutic dose. In some embodiments, the dose of the DPP IV inhibitor is from about 30% to about 35% of the lowest diabetes therapeutic dose.

In some embodiments, the dose of the DPP IV inhibitor is from about 35% to about 50% of the lowest diabetes therapeutic dose. In some embodiments, the dose of the DPP IV inhibitor is from about 35% to about 45% of the lowest diabetes therapeutic dose. In some embodiments, the dose of the DPP IV inhibitor is from about 35% to about 40% of the lowest diabetes therapeutic dose.

In some embodiments, the dose of the DPP IV inhibitor is from about 40% to about 50% of the lowest diabetes therapeutic dose. In some embodiments, the dose of the DPP IV inhibitor is from about 45% to about 50% of the lowest diabetes therapeutic dose.

In some embodiments, the dose of the biguanide is from about 20% to about 50% of the lowest diabetes therapeutic dose. In some embodiments, the dose of the biguanide is from about 20% to about 45% of the lowest diabetes therapeutic dose. In some embodiments, the dose of the biguanide is from about 20% to about 40% of the lowest diabetes therapeutic dose. In some embodiments, the dose of the biguanide is from about 20% to about 35% of the lowest diabetes therapeutic dose. In some embodiments, the dose of the biguanide is from about 20% to about 30% of the lowest diabetes therapeutic dose. In some embodiments, the dose of the biguanide is from about 20% to about 25% of the lowest diabetes therapeutic dose.

In some embodiments, the dose of the biguanide is from about 25% to about 50% of the lowest diabetes therapeutic dose. In some embodiments, the dose of the biguanide is from about 25% to about 45% of the lowest diabetes therapeutic dose. In some embodiments, the dose of the biguanide is from about 25% to about 40% of the lowest diabetes therapeutic dose. In some embodiments, the dose of the biguanide is from about 25% to about 35% of the lowest diabetes therapeutic dose. In some embodiments, the dose of the biguanide is from about 25% to about 30% of the lowest diabetes therapeutic dose.

In some embodiments, the dose of the biguanide is from about 30% to about 50% of the lowest diabetes therapeutic dose. In some embodiments, the dose of the biguanide is from about 30% to about 45% of the lowest diabetes therapeutic dose. In some embodiments, the dose of the biguanide is from about 30% to about 40% of the lowest diabetes therapeutic dose. In some embodiments, the dose of the biguanide is from about 30% to about 35% of the lowest diabetes therapeutic dose.

In some embodiments, the dose of the biguanide is from about 35% to about 50% of the lowest diabetes therapeutic dose. In some embodiments, the dose of the biguanide is from about 35% to about 45% of the lowest diabetes therapeutic dose. In some embodiments, the dose of the biguanide is from about 35% to about 40% of the lowest diabetes therapeutic dose.

In some embodiments, the dose of the biguanide is from about 40% to about 50% of the lowest diabetes therapeutic dose. In some embodiments, the dose of the biguanide is from about 45% to about 50% of the lowest diabetes therapeutic dose.

In some embodiments, the dose of the SGLT2 inhibitor is from about 20% to about 50% of the lowest diabetes therapeutic dose. In some embodiments, the dose of the SGLT2 inhibitor is from about 20% to about 45% of the lowest diabetes therapeutic dose. In some embodiments, the dose of the SGLT2 inhibitor is from about 20% to about 40% of the lowest diabetes therapeutic dose. In some embodiments, the dose of the SGLT2 inhibitor is from about 20% to about 35% of the lowest diabetes therapeutic dose. In some embodiments, the dose of the SGLT2 inhibitor is from about 20% to about 30% of the lowest diabetes therapeutic dose. In some embodiments, the dose of the SGLT2 inhibitor is from about 20% to about 25% of the lowest diabetes therapeutic dose.

In some embodiments, the dose of the SGLT2 inhibitor is from about 25% to about 50% of the lowest diabetes therapeutic dose. In some embodiments, the dose of the SGLT2 inhibitor is from about 25% to about 45% of the lowest diabetes therapeutic dose. In some embodiments, the dose of the SGLT2 inhibitor is from about 25% to about 40% of the lowest diabetes therapeutic dose. In some embodiments, the dose of the SGLT2 inhibitor is from about 25% to about 35% of the lowest diabetes therapeutic dose. In some embodiments, the dose of the SGLT2 inhibitor is from about 25% to about 30% of the lowest diabetes therapeutic dose.

In some embodiments, the dose of the SGLT2 inhibitor is from about 30% to about 50% of the lowest diabetes therapeutic dose. In some embodiments, the dose of the SGLT2 inhibitor is from about 30% to about 45% of the lowest diabetes therapeutic dose. In some embodiments, the dose of the SGLT2 inhibitor is from about 30% to about 40% of the lowest diabetes therapeutic dose. In some embodiments, the dose of the SGLT2 inhibitor is from about 30% to about 35% of the lowest diabetes therapeutic dose.

In some embodiments, the dose of the SGLT2 inhibitor is from about 35% to about 50% of the lowest diabetes therapeutic dose. In some embodiments, the dose of the SGLT2 inhibitor is from about 35% to about 45% of the lowest diabetes therapeutic dose. In some embodiments, the dose of the SGLT2 inhibitor is from about 35% to about 40% of the lowest diabetes therapeutic dose.

In some embodiments, the dose of the SGLT2 inhibitor is from about 40% to about 50% of the lowest diabetes therapeutic dose. In some embodiments, the dose of the SGLT2 inhibitor is from about 45% to about 50% of the lowest diabetes therapeutic dose.

In some embodiments, the dose of each of the DPP IV inhibitor, the biguanide, and the SGLT2 inhibitor is from about 20% to about 40% of the lowest diabetes therapeutic dose.

In some embodiments, the dose of each of the DPP IV inhibitor, the biguanide, and the SGLT2 inhibitor is from about 20% to about 30% of the lowest diabetes therapeutic dose.

In some embodiments, the dose of the DPP IV inhibitor is about 20%, about 21%, about 22, about 23%, about 24%, about 25%, about 26%, about 27%, about 28%, about 29%, or about 30% of the lowest diabetes therapeutic dose. In some embodiments, the dose of the DPP IV inhibitor is about 25% of the lowest diabetes therapeutic dose. In some embodiments, the DPP IV inhibitor is sitagliptin. In some embodiments, the dose of sitagliptin is about 5.0, about 5.25, about 5.5, about 5.75, about 6.0, about 6.25, about 6.5, about 6.75, about 7.0, about 7.25, or about 7.5 mg.

In some embodiments, the dose of the biguanide inhibitor is about 20%, about 21%, about 22, about 23%, about 24%, about 25%, about 26%, about 27%, about 28%, about 29%, or about 30% of the lowest diabetes therapeutic dose. In some embodiments, the dose of the biguanide is about 25% of the lowest diabetes therapeutic dose. In some embodiments, the biguanide is metformin or metformin hydrochloride. In some embodiments, the dose of metformin or metformin hydrochloride is about 100, about 105, about, 110, about 115, about 120, about 125, about 130, about 135, about 140, about 145, or about 150 mg.

In some embodiments, the dose of the SGLT2 inhibitor is about 20%, about 21%, about 22, about 23%, about 24%, about 25%, about 26%, about 27%, about 28%, about 29%, or about 30% of the lowest diabetes therapeutic dose. In some embodiments, the dose of the SGLT2 inhibitor is about 25% of the lowest diabetes therapeutic dose. In some embodiments, the SGLT2 inhibitor is dapagliflozin. In some embodiments, the SGLT2 inhibitor is dapagliflozin. In some embodiments, the dose of dapagliflozin is about 1.0, about 1.1, about 1.2, about 1.3, about 1.4, or about 1.5 mg. In some embodiments, the SGLT2 inhibitor is empagliflozin. In some embodiments, the dose of empagliflozin is about 2.0, about 2.1, about 2.2, about 2.3, about 2.4, about 2.5, about 2.6, about 2.7, about 2.8, about 2.9, or about 3.0 mg.

In some embodiments, the lowest diabetes therapeutic dose (LDTD) and the corresponding proposed dose and proposed dose range for the following compounds are as described in Table 1.

TABLE 1

| Agent | Lowest Diabetes Therapeutic Dose (LDTD) (mg) | Proposed Dose (mg) 25% LDTD | Proposed Dose Range 20%-30% LDTD (mg) |
|---|---|---|---|
| sitagliptin | 25 | 6.25 | 5.0-7.5 |
| vildagliptin | 50 | 12.5 | 10-15 |
| saxagliptin | 2.5 | 0.625 | 0.5-0.75 |
| linagliptin | 5.0 | 1.25 | 1.0-1.5 |
| alogliptin | 6.25 | 1.5625 | 1.25-1.875 |
| metformin | 500 | 125 | 100-150 |
| dapagliflozin | 5.0 | 1.25 | 1.0-1.5 |
| empagliflozin | 10.0 | 2.5 | 2.0-3.0 |
| canagliflozin | 100 | 25 | 20-30 |
| ertugliflozin | 5.0 | 1.25 | 1.0-1.5 |

In some embodiments, the pharmaceutical composition comprises: (a) sitagliptin as a DPP IV inhibitor; (b) metformin as a biguanide; and (c) dapagliflozin as an SGLT2 inhibitor. In some embodiments, the pharmaceutical composition comprises: (a) sitagliptin as a DPP IV inhibitor; (b) metformin as a biguanide; and (c) empagliflozin as an SGLT2 inhibitor. In some embodiments, the dose of sitagliptin is from about 5 mg to about 7.5 mg, the dose of metformin is from about 100 mg to about 150 mg, and the dose of dapagliflozin is from about 1.0 mg to about 1.5 mg. In some embodiments, the dose of sitagliptin is from about 5 mg to about 7.5 mg, the dose of metformin is from about 100 mg to about 150 mg, and the dose of empagliflozin is from about 2.0 mg to about 3.0 mg.

In some embodiments, the dose of each of (a) a DPP IV inhibitor; (b) a biguanide; and (c) an SGLT2 inhibitor is about 25% of the lowest diabetes therapeutic dose (LDTD) for each of (a), (b), and (c). In some embodiments, the dose of sitagliptin is about 6.25 mg, the dose of metformin is about 125 mg, and the dose of dapagliflozin is about 1.25 mg. In some embodiments, the dose of sitagliptin is about 6.25 mg, the dose of metformin is about 125 mg, and the dose of empagliflozin is about 2.5 mg. In some embodiments, the metformin is metformin hydrochloride.

In some embodiments, the dose of each of the DPP IV inhibitor, the biguanide, and the SGLT2 inhibitor is from about 30% to about 40% of the lowest diabetes therapeutic dose.

In some embodiments, the dose of the DPP IV inhibitor is about 30%, about 31%, about 32%, about 33%, about 34%, about 35%, about 36%, about 37%, about 38%, about 39%, or about 40% of the lowest diabetes therapeutic dose. In some embodiments, the dose of the DPP IV inhibitor is about 33% of the lowest diabetes therapeutic dose. In some embodiments, the DPP IV inhibitor is sitagliptin. In some embodiments, the dose of sitagliptin is about 7.5, about 7.75, about 8.0, about 8.25, about 8.5, about 8.75, about 9.0, about 9.25, about 9.5, about 9.75, or about 10 mg.

In some embodiments, the dose of the biguanide inhibitor is about 30%, about 31%, about 32%, about 33%, about 34%, about 35%, about 36%, about 37%, about 38%, about 39%, or about 40% of the lowest diabetes therapeutic dose. In some embodiments, the dose of the biguanide is about 33% of the lowest diabetes therapeutic dose. In some embodiments, the biguanide is metformin or metformin hydrochloride. In some embodiments, the dose of metformin or metformin hydrochloride is about 150, about 155, about 160, about 165, about 170, about 175, about 180, about 185, about 190, about 195, or about 200 mg.

In some embodiments, the dose of the SGLT2 inhibitor is about 30%, about 31%, about 32%, about 33%, about 34%, about 35%, about 36%, about 37%, about 38%, about 39%, or about 40% of the lowest diabetes therapeutic dose. In some embodiments, the dose of the SGLT2 inhibitor is about 33% of the lowest diabetes therapeutic dose. In some embodiments, the SGLT2 inhibitor is dapagliflozin. In some embodiments, the dose of dapagliflozin is about 1.5, about 1.55, about 1.6, about 1.65, about 1.7, about 1.75, about 1.8, about 1.85, about 1.9, about 1.95, or about 2.0 mg. In some embodiments, the SGLT2 inhibitor is empagliflozin. In some embodiments, the dose of empagliflozin is about 3.0, about 3.1, about 3.2, about 3.3, about 3.4, about 3.5, about 3.6, about 3.7, about 3.8, about 3.9, or about 4.0 mg.

In some embodiments, the lowest diabetes therapeutic dose (LDTD) and the corresponding proposed dose and proposed dose range for the following compounds are as described in Table 2.

TABLE 2

| Agent | Lowest Diabetes Therapeutic Dose (LDTD) (mg) | Proposed Dose (mg) 33% LDTD | Proposed Dose Range 30%-40% LDTD (mg) |
|---|---|---|---|
| sitagliptin | 25 | 8.25 | 7.5-10 |
| vildagliptin | 50 | 16.5 | 15-20 |
| saxagliptin | 2.5 | 0.825 | 0.75-1 |
| linagliptin | 5.0 | 1.65 | 1.5-2 |
| alogliptin | 6.25 | 2.0625 | 1.875-2.5 |
| metformin | 500 | 165 | 150-200 |
| dapagliflozin | 5.0 | 1.65 | 1.5-2.0 |
| empagliflozin | 10.0 | 3.3 | 3.0-4.0 |
| canagliflozin | 100 | 33 | 30-40 |
| ertugliflozin | 5.0 | 1.65 | 1.5-2.0 |

In some embodiments, the pharmaceutical composition comprises: (a) sitagliptin as a DPP IV inhibitor; (b) metformin as a biguanide; and (c) dapagliflozin as an SGLT2 inhibitor. In some embodiments, the pharmaceutical composition comprises: (a) sitagliptin as a DPP IV inhibitor; (b) metformin as a biguanide; and (c) empagliflozin as an SGLT2 inhibitor. In some embodiments, the dose of sitagliptin is from about 7.5 mg to about 10 mg, the dose of metformin is from about 150 mg to about 200 mg, and the dose of dapagliflozin is from about 1.5 mg to about 2.0 mg. In some embodiments, the dose of sitagliptin is from about 7.5 mg to about 10 mg, the dose of metformin is from about 150 mg to about 200 mg, and the dose of empagliflozin is from about 3.0 mg to about 4.0 mg.

In some embodiments, the dose of each of (a) a DPP IV inhibitor; (b) a biguanide; and (c) an SGLT2 inhibitor is about 33% of the lowest diabetes therapeutic dose (LDTD) for each of (a), (b), and (c). In some embodiments, the dose of sitagliptin is about 8.25 mg, the dose of metformin is about 165 mg, and the dose of dapagliflozin is about 1.65 mg. In some embodiments, the metformin is metformin hydrochloride. In some embodiments, the dose of sitagliptin is about 8.25 mg, the dose of metformin is about 165 mg, and the dose of empagliflozin is about 3.3 mg.

In some embodiments, the dose of the DPP IV inhibitor is from about 40% to about 75% of the lowest diabetes therapeutic dose. In some embodiments, the dose of the DPP IV inhibitor is from about 40% to about 70% of the lowest diabetes therapeutic dose. In some embodiments, the dose of the DPP IV inhibitor is from about 40% to about 65% of the lowest diabetes therapeutic dose. In some embodiments, the dose of the DPP IV inhibitor is from about 40% to about 60% of the lowest diabetes therapeutic dose. In some embodiments, the dose of the DPP IV inhibitor is from about 40% to about 55% of the lowest diabetes therapeutic dose. In some embodiments, the dose of the DPP IV inhibitor is from about 40% to about 50% of the lowest diabetes therapeutic dose. In some embodiments, the dose of the DPP IV inhibitor is from about 40% to about 45% of the lowest diabetes therapeutic dose.

In some embodiments, the dose of the DPP IV inhibitor is from about 45% to about 75% of the lowest diabetes therapeutic dose. In some embodiments, the dose of the DPP IV inhibitor is from about 45% to about 70% of the lowest diabetes therapeutic dose. In some embodiments, the dose of the DPP IV inhibitor is from about 45% to about 65% of the lowest diabetes therapeutic dose. In some embodiments, the dose of the DPP IV inhibitor is from about 45% to about 60% of the lowest diabetes therapeutic dose. In some embodiments, the dose of the DPP IV inhibitor is from about 45% to about 55% of the lowest diabetes therapeutic dose. In some embodiments, the dose of the DPP IV inhibitor is from about 45% to about 50% of the lowest diabetes therapeutic dose.

In some embodiments, the dose of the DPP IV inhibitor is from about 50% to about 75% of the lowest diabetes therapeutic dose. In some embodiments, the dose of the DPP IV inhibitor is from about 50% to about 70% of the lowest diabetes therapeutic dose. In some embodiments, the dose of the DPP IV inhibitor is from about 50% to about 65% of the lowest diabetes therapeutic dose. In some embodiments, the dose of the DPP IV inhibitor is from about 50% to about 60% of the lowest diabetes therapeutic dose. In some embodiments, the dose of the DPP IV inhibitor is from about 50% to about 55% of the lowest diabetes therapeutic dose.

In some embodiments, the dose of the DPP IV inhibitor is from about 55% to about 75% of the lowest diabetes therapeutic dose. In some embodiments, the dose of the DPP IV inhibitor is from about 55% to about 70% of the lowest diabetes therapeutic dose. In some embodiments, the dose of the DPP IV inhibitor is from about 55% to about 65% of the lowest diabetes therapeutic dose. In some embodiments, the dose of the DPP IV inhibitor is from about 55% to about 60% of the lowest diabetes therapeutic dose.

In some embodiments, the dose of the DPP IV inhibitor is from about 60% to about 75% of the lowest diabetes therapeutic dose. In some embodiments, the dose of the DPP IV inhibitor is from about 60% to about 70% of the lowest diabetes therapeutic dose. In some embodiments, the dose of the DPP IV inhibitor is from about 60% to about 65% of the lowest diabetes therapeutic dose.

In some embodiments, the dose of the DPP IV inhibitor is from about 65% to about 75% of the lowest diabetes therapeutic dose. In some embodiments, the dose of the DPP IV inhibitor is from about 65% to about 70% of the lowest diabetes therapeutic dose. In some embodiments, the dose of the DPP IV inhibitor is from about 70% to about 75% of the lowest diabetes therapeutic dose.

In some embodiments, the dose of the biguanide is from about 40% to about 75% of the lowest diabetes therapeutic dose. In some embodiments, the dose of the biguanide is from about 40% to about 70% of the lowest diabetes therapeutic dose. In some embodiments, the dose of the biguanide is from about 40% to about 65% of the lowest diabetes therapeutic dose. In some embodiments, the dose of the biguanide is from about 40% to about 60% of the lowest diabetes therapeutic dose. In some embodiments, the dose of the biguanide is from about 40% to about 55% of the lowest diabetes therapeutic dose. In some embodiments, the dose of the biguanide is from about 40% to about 50% of the lowest diabetes therapeutic dose. In some embodiments, the dose of the biguanide is from about 40% to about 45% of the lowest diabetes therapeutic dose.

In some embodiments, the dose of the biguanide is from about 45% to about 75% of the lowest diabetes therapeutic dose. In some embodiments, the dose of the biguanide is from about 45% to about 70% of the lowest diabetes therapeutic dose. In some embodiments, the dose of the biguanide is from about 45% to about 65% of the lowest diabetes therapeutic dose. In some embodiments, the dose of the biguanide is from about 45% to about 60% of the lowest diabetes therapeutic dose. In some embodiments, the dose of the biguanide is from about 45% to about 55% of the lowest diabetes therapeutic dose. In some embodiments, the dose of the biguanide is from about 45% to about 50% of the lowest diabetes therapeutic dose.

In some embodiments, the dose of the biguanide is from about 50% to about 75% of the lowest diabetes therapeutic dose. In some embodiments, the dose of the biguanide is from about 50% to about 70% of the lowest diabetes therapeutic dose. In some embodiments, the dose of the biguanide is from about 50% to about 65% of the lowest diabetes therapeutic dose. In some embodiments, the dose of the biguanide is from about 50% to about 60% of the lowest diabetes therapeutic dose. In some embodiments, the dose of the biguanide is from about 50% to about 55% of the lowest diabetes therapeutic dose.

In some embodiments, the dose of the biguanide is from about 55% to about 75% of the lowest diabetes therapeutic dose. In some embodiments, the dose of the biguanide is from about 55% to about 70% of the lowest diabetes therapeutic dose. In some embodiments, the dose of the biguanide is from about 55% to about 65% of the lowest diabetes therapeutic dose. In some embodiments, the dose of the biguanide is from about 55% to about 60% of the lowest diabetes therapeutic dose.

In some embodiments, the dose of the biguanide is from about 60% to about 75% of the lowest diabetes therapeutic dose. In some embodiments, the dose of the biguanide is from about 60% to about 70% of the lowest diabetes therapeutic dose. In some embodiments, the dose of the biguanide is from about 60% to about 65% of the lowest diabetes therapeutic dose.

In some embodiments, the dose of the biguanide is from about 65% to about 75% of the lowest diabetes therapeutic dose. In some embodiments, the dose of the biguanide is from about 65% to about 70% of the lowest diabetes therapeutic dose. In some embodiments, the dose of the biguanide is from about 70% to about 75% of the lowest diabetes therapeutic dose.

In some embodiments, the dose of the SGLT2 inhibitor is from about 40% to about 75% of the lowest diabetes therapeutic dose. In some embodiments, the dose of the SGLT2 inhibitor is from about 40% to about 70% of the lowest diabetes therapeutic dose. In some embodiments, the dose of the SGLT2 inhibitor is from about 40% to about 65% of the lowest diabetes therapeutic dose. In some embodiments, the dose of the SGLT2 inhibitor is from about 40% to about 60% of the lowest diabetes therapeutic dose. In some embodiments, the dose of the SGLT2 inhibitor is from about 40% to about 55% of the lowest diabetes therapeutic dose. In some embodiments, the dose of the SGLT2 inhibitor is from about 40% to about 50% of the lowest diabetes therapeutic dose. In some embodiments, the dose of the SGLT2 inhibitor is from about 40% to about 45% of the lowest diabetes therapeutic dose.

In some embodiments, the dose of the SGLT2 inhibitor is from about 45% to about 75% of the lowest diabetes therapeutic dose. In some embodiments, the dose of the SGLT2 inhibitor is from about 45% to about 70% of the lowest diabetes therapeutic dose. In some embodiments, the dose of the SGLT2 inhibitor is from about 45% to about 65% of the lowest diabetes therapeutic dose. In some embodiments, the dose of the SGLT2 inhibitor is from about 45% to about 60% of the lowest diabetes therapeutic dose. In some embodiments, the dose of the SGLT2 inhibitor is from about 45% to about 55% of the lowest diabetes therapeutic dose. In some embodiments, the dose of the SGLT2 inhibitor is from about 45% to about 50% of the lowest diabetes therapeutic dose.

In some embodiments, the dose of the SGLT2 inhibitor is from about 50% to about 75% of the lowest diabetes therapeutic dose. In some embodiments, the dose of the SGLT2 inhibitor is from about 50% to about 70% of the lowest diabetes therapeutic dose. In some embodiments, the dose of the SGLT2 inhibitor is from about 50% to about 65% of the lowest diabetes therapeutic dose. In some embodiments, the dose of the SGLT2 inhibitor is from about 50% to about 60% of the lowest diabetes therapeutic dose. In some embodiments, the dose of the SGLT2 inhibitor is from about 50% to about 55% of the lowest diabetes therapeutic dose.

In some embodiments, the dose of the SGLT2 inhibitor is from about 55% to about 75% of the lowest diabetes therapeutic dose. In some embodiments, the dose of the SGLT2 inhibitor is from about 55% to about 70% of the lowest diabetes therapeutic dose. In some embodiments, the dose of the SGLT2 inhibitor is from about 55% to about 65% of the lowest diabetes therapeutic dose. In some embodiments, the dose of the SGLT2 inhibitor is from about 55% to about 60% of the lowest diabetes therapeutic dose.

In some embodiments, the dose of the SGLT2 inhibitor is from about 60% to about 75% of the lowest diabetes therapeutic dose. In some embodiments, the dose of the SGLT2 inhibitor is from about 60% to about 70% of the lowest diabetes therapeutic dose. In some embodiments, the dose of the SGLT2 inhibitor is from about 60% to about 65% of the lowest diabetes therapeutic dose.

In some embodiments, the dose of the SGLT2 inhibitor is from about 65% to about 75% of the lowest diabetes therapeutic dose. In some embodiments, the dose of the SGLT2 inhibitor is from about 65% to about 70% of the lowest diabetes therapeutic dose. In some embodiments, the dose of the SGLT2 inhibitor is from about 70% to about 75% of the lowest diabetes therapeutic dose.

In some embodiments, the dose of the SGLT2 inhibitor is from about 40% to about 75% of the lowest diabetes therapeutic dose. In some embodiments, the dose of the SGLT2 inhibitor is from about 40% to about 70% of the lowest diabetes therapeutic dose. In some embodiments, the dose of the SGLT2 inhibitor is from about 40% to about 65% of the lowest diabetes therapeutic dose. In some embodiments, the dose of the SGLT2 inhibitor is from about 40% to about 60% of the lowest diabetes therapeutic dose. In some embodiments, the dose of the SGLT2 inhibitor is from about 40% to about 55% of the lowest diabetes therapeutic dose. In some embodiments, the dose of the SGLT2 inhibitor is from about 40% to about 50% of the lowest diabetes therapeutic dose. In some embodiments, the dose of the SGLT2 inhibitor is from about 40% to about 45% of the lowest diabetes therapeutic dose.

In some embodiments, the dose of the SGLT2 inhibitor is from about 45% to about 75% of the lowest diabetes therapeutic dose. In some embodiments, the dose of the SGLT2 inhibitor is from about 45% to about 70% of the lowest diabetes therapeutic dose. In some embodiments, the dose of the SGLT2 inhibitor is from about 45% to about 65% of the lowest diabetes therapeutic dose. In some embodiments, the dose of the SGLT2 inhibitor is from about 45% to about 60% of the lowest diabetes therapeutic dose. In some embodiments, the dose of the SGLT2 inhibitor is from about 45% to about 55% of the lowest diabetes therapeutic dose. In some embodiments, the dose of the SGLT2 inhibitor is from about 45% to about 50% of the lowest diabetes therapeutic dose.

In some embodiments, the dose of the SGLT2 inhibitor is from about 50% to about 75% of the lowest diabetes therapeutic dose. In some embodiments, the dose of the SGLT2 inhibitor is from about 50% to about 70% of the lowest diabetes therapeutic dose. In some embodiments, the dose of the SGLT2 inhibitor is from about 50% to about 65% of the lowest diabetes therapeutic dose. In some embodiments, the dose of the SGLT2 inhibitor is from about 50% to about 60% of the lowest diabetes therapeutic dose. In some embodiments, the dose of the SGLT2 inhibitor is from about 50% to about 55% of the lowest diabetes therapeutic dose.

In some embodiments, the dose of the SGLT2 inhibitor is from about 55% to about 75% of the lowest diabetes therapeutic dose. In some embodiments, the dose of the SGLT2 inhibitor is from about 55% to about 70% of the lowest diabetes therapeutic dose. In some embodiments, the dose of the SGLT2 inhibitor is from about 55% to about 65% of the lowest diabetes therapeutic dose. In some embodiments, the dose of the SGLT2 inhibitor is from about 55% to about 60% of the lowest diabetes therapeutic dose.

In some embodiments, the dose of the SGLT2 inhibitor is from about 60% to about 75% of the lowest diabetes therapeutic dose. In some embodiments, the dose of the SGLT2 inhibitor is from about 60% to about 70% of the lowest diabetes therapeutic dose. In some embodiments, the dose of the SGLT2 inhibitor is from about 60% to about 65% of the lowest diabetes therapeutic dose.

In some embodiments, the dose of the SGLT2 inhibitor is from about 65% to about 75% of the lowest diabetes therapeutic dose. In some embodiments, the dose of the SGLT2 inhibitor is from about 65% to about 70% of the lowest diabetes therapeutic dose. In some embodiments, the dose of the SGLT2 inhibitor is from about 70% to about 75% of the lowest diabetes therapeutic dose.

In some embodiments, the dose of each of the DPP IV inhibitor, the biguanide, and the SGLT2 inhibitor is from about 40% to about 60% of the lowest diabetes therapeutic dose.

In some embodiments, the dose of each of the DPP IV inhibitor, the biguanide, and the SGLT2 inhibitor is from about 40% to about 50% of the lowest diabetes therapeutic dose.

In some embodiments, the dose of each of the DPP IV inhibitor, the biguanide, and the SGLT2 inhibitor is from about 50% to about 60% of the lowest diabetes therapeutic dose.

In some embodiments, the dose of each of the DPP IV inhibitor, the biguanide, and the SGLT2 inhibitor is from about 45% to about 55% of the lowest diabetes therapeutic dose.

In some embodiments, the dose of the DPP IV inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest diabetes therapeutic dose. In some embodiments, the dose of the DPP IV inhibitor is about 50% of the lowest diabetes therapeutic dose. In some embodiments, the DPP IV inhibitor is sitagliptin. In some embodiments, the dose of sitagliptin is about 10, about 10.25, about 10.5, about 10.75, about 11, about 11.25, about 11.5, about 11.75, about 12, about 12.25, about 12.5, about 12.75, about 13, about 13.25, about 13.5, about 13.75, about 14, about 14.25, about 14.5, about 14.75, or about 15 mg.

In some embodiments, the dose of the biguanide inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest diabetes therapeutic dose. In some embodiments, the dose of the biguanide is about 50% of the lowest diabetes therapeutic dose. In some embodiments, the biguanide is metformin or metformin hydrochloride. In some embodiments, the dose of metformin or metformin hydrochloride is about 200, about 205, about 210, about 215, about 220, about 225, about 230, about 235, about 240, about 245, about 250, about 255, about 260, about 265, about 270, about 275, about 280, about 285, about 290, about 295, or about 300 mg.

In some embodiments, the dose of the SGLT2 inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest diabetes therapeutic dose. In some embodiments, the dose of the SGLT2 inhibitor is about 50% of the lowest diabetes therapeutic dose. In some embodiments, the SGLT2 inhibitor is dapagliflozin. In some embodiments, the dose of dapagliflozin is about 2.0, about 2.1, about 2.2, about 2.3, about 2.4, about 2.5, about 2.6, about 2.7, about 2.8, about 2.9, or about 3.0 mg. In some embodiments, the dose of dapagliflozin is about 2.0, about 2.25, about 2.5, about 2.75, or about 3.0 mg. In some embodiments, the SGLT2 inhibitor is empagliflozin. In some embodiments, the dose of empagliflozin is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0 mg.

In some embodiments, the lowest diabetes therapeutic dose (LDTD) and the corresponding proposed dose and proposed dose range for the following compounds are as described in Table 3.

TABLE 3

| Agent | Lowest Diabetes Therapeutic Dose (LDTD) (mg) | Proposed Dose (mg) 50% LDTD | Proposed Dose Range 40%-60% LDTD (mg) | Proposed Dose Range 45%-55% LDTD (mg) |
|---|---|---|---|---|
| sitagliptin | 25 | 12.5 | 10-15 | 11.25-12.5 |
| vildagliptin | 50 | 25 | 20-30 | 22.5-27.5 |
| saxagliptin | 2.5 | 1.25 | 1-1.5 | 1.125-1.375 |
| linagliptin | 5.0 | 2.5 | 2-3 | 2.25-2.75 |
| alogliptin | 6.25 | 3.125 | 2.5-3.75 | 2.8125-3.4375 |
| metformin | 500 | 250 | 200-300 | 225-275 |
| dapagliflozin | 5.0 | 2.5 | 2-3 | 2.25-2.75 |
| empagliflozin | 10.0 | 5.0 | 4.0-6.0 | 4.5-5.5 |
| canagliflozin | 100 | 50 | 40-50 | 45-55 |
| ertugliflozin | 5.0 | 2.5 | 2-3 | 2.25-2.75 |

In some embodiments, the pharmaceutical composition comprises: (a) sitagliptin as a DPP IV inhibitor; (b) metformin as a biguanide; and (c) dapagliflozin as an SGLT2 inhibitor. In some embodiments, the dose of sitagliptin is from about 10 mg to about 15 mg, the dose of metformin is from about 200 mg to about 300 mg, and the dose of dapagliflozin is from about 2.0 to about 3.0 mg. In some embodiments, the dose of sitagliptin is from about 10 mg to about 15 mg, the dose of metformin is from about 200 mg to about 300 mg, and the dose of empagliflozin is from about 4.0 to about 6.0 mg.

In some embodiments, the dose of sitagliptin is from about 11.25 mg to about 12.5 mg, the dose of metformin is from about 225 mg to about 275 mg, and the dose of dapagliflozin is from about 2.25 to about 2.75 mg. In some embodiments, the dose of sitagliptin is from about 11.25 mg to about 12.5 mg, the dose of metformin is from about 225 mg to about 275 mg, and the dose of empagliflozin is from about 4.5 to about 5.5 mg.

In some embodiments, the dose of each of (a) a DPP IV inhibitor; (b) a biguanide; and (c) an SGLT2 inhibitor is about 50% of the lowest diabetes therapeutic dose (LDTD) for each of (a), (b), and (c). In some embodiments, the dose of sitagliptin is about 12.5 mg, the dose of metformin is about 250 mg, and the dose of dapagliflozin is about 2.5 mg. In some embodiments, the dose of sitagliptin is about 12.5 mg, the dose of metformin is about 250 mg, and the dose of empagliflozin is about 5.0 mg. In some embodiments, the metformin is metformin hydrochloride.

In some embodiments, the dose of the DPP IV inhibitor is from about 60% to about 75% of the lowest diabetes therapeutic dose.

In some embodiments, the dose of the DPP IV inhibitor is about 60%, about 61%, about 62%, about 63%, about 64%, about 65%, about 66%, about 67%, about 68%, about 69%, about 70%, about 71%, about 72%, about 73%, about 74%, or about 75% of the lowest diabetes therapeutic dose. In some embodiments, the dose of the DPP IV inhibitor is about 70% of the lowest diabetes therapeutic dose. In some embodiments, the DPP IV inhibitor is sitagliptin. In some embodiments, the dose of sitagliptin is about 15, about 15.25, about 15.5, about 15.75, about 16, about 16.25, about 16.5, about 16.75, about 17, about 17.25, about 17.5, about 17.75, about 18, about 18.25, about 18.5, or about 18.75 mg.

In some embodiments, the dose of the biguanide is from about 60% to about 75% of the lowest diabetes therapeutic dose. In some embodiments, the dose of the biguanide inhibitor is about 60%, about 61%, about 62%, about 63%, about 64%, about 65%, about 66%, about 67%, about 68%, about 69%, about 70%, about 71%, about 72%, about 73%, about 74%, or about 75% of the lowest diabetes therapeutic dose. In some embodiments, the dose of the biguanide is about 70% of the lowest diabetes therapeutic dose. In some embodiments, the biguanide is metformin or metformin hydrochloride. In some embodiments, the dose of metformin or metformin hydrochloride is about 300, about 305, about 310, about 315, about 320, about 325, about 330, about 335, about 340, about 345, about 350, about 355, about 360, about 365, about 370, or about 375 mg.

In some embodiments, the dose of the SGLT2 inhibitor is from about 60% to about 75% of the lowest diabetes therapeutic dose.

In some embodiments, the dose of the SGLT2 inhibitor is about 60%, about 61%, about 62%, about 63%, about 64%, about 65%, about 66%, about 67%, about 68%, about 69%, about 70%, about 71%, about 72%, about 73%, about 74%, or about 75% of the lowest diabetes therapeutic dose. In some embodiments, the dose of the SGLT2 inhibitor is about 70% of the lowest diabetes therapeutic dose. In some embodiments, the SGLT2 inhibitor is dapagliflozin. In some embodiments, the dose of dapagliflozin is about 3.0, about 3.05, about 3.10, about 3.15, 3.20, about 3.25, about 3.30, about 3.35, about 3.40, about 3.45, about 3.5, about 3.55, about 3.60, about 3.65, about 3.70, or about 3.75 mg. In some embodiments, the SGLT2 inhibitor is empagliflozin. In some embodiments, the dose of empagliflozin is about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5 mg.

In some embodiments, the lowest diabetes therapeutic dose (LDTD) and the corresponding proposed dose and proposed dose range for the following compounds are as described in Table 4.

TABLE 4

| Agent | Lowest Diabetes Therapeutic Dose (LDTD) (mg) | Proposed Dose (mg) 70% LDTD | Proposed Dose Range 60%-75% LDTD (mg) | Proposed Dose Range 60%-70% LDTD (mg) |
|---|---|---|---|---|
| sitagliptin | 25 | 17.5 | 15-18.75 | 15-7.5 |
| vildagliptin | 50 | 35 | 30-37.5 | 30-35 |
| saxagliptin | 2.5 | 1.75 | 1.5-1.875 | 1.5-1.75 |
| linagliptin | 5.0 | 3.5 | 3-3.75 | 3-3.5 |
| alogliptin | 6.25 | 4.375 | 3.75-4.6875 | 3.75-4.375 |
| metformin | 500 | 350 | 300-375 | 300-350 |
| dapagliflozin | 5.0 | 3.5 | 3.0-3.75 | 3.0-3.5 |
| empagliflozin | 10.0 | 7.0 | 6.0-7.5 | 6.0-7.0 |
| canagliflozin | 100 | 70 | 60-75 | 60-70 |
| ertugliflozin | 5.0 | 3.5 | 3.0-3.75 | 3.0-3.5 |

In some embodiments, the pharmaceutical composition comprises: (a) sitagliptin as a DPP IV inhibitor; (b) metformin as a biguanide; and (c) dapagliflozin as an SGLT2 inhibitor. In some embodiments, the pharmaceutical composition comprises: (a) sitagliptin as a DPP IV inhibitor; (b) metformin as a biguanide; and (c) empagliflozin as an SGLT2 inhibitor. In some embodiments, the dose of sitagliptin is from about 15 mg to about 18.75 mg, the dose of metformin is from about 300 mg to about 375 mg, and the dose of dapagliflozin is from about 3.0 mg to about 3.75 mg. In some embodiments, the dose of sitagliptin is from about 15 mg to about 17.5 mg, the dose of metformin is from about 300 mg to about 350 mg, and the dose of empagliflozin is from about 6.0 mg to about 7.5 mg.

In some embodiments, the dose of sitagliptin is from about 15 mg to about 17.5 mg, the dose of metformin is from about 300 mg to about 350 mg, and the dose of dapagliflozin is from about 3.0 mg to about 3.5 mg. In some embodiments, the dose of sitagliptin is from about 15 mg to about 17.5 mg, the dose of metformin is from about 300 mg to about 350 mg, and the dose of empagliflozin is from about 6.0 mg to about 7.0 mg.

In some embodiments, the dose of (a) a DPP IV inhibitor; (b) a biguanide; and (c) an SGLT2 inhibitor is about 70% of the lowest diabetes therapeutic dose (LDTD) for each of (a), (b), and (c). In some embodiments, the dose of sitagliptin is about 17.5 mg, the dose of metformin is about 350 mg, and the dose of dapagliflozin is about 3.5 mg. In some embodiments, the dose of sitagliptin is about 17.5 mg, the dose of metformin is about 350 mg, and the dose of empagliflozin is about 7.0 mg. In some embodiments, metformin is metformin hydrochloride.

In some embodiments, the dose of (a) a DPP IV inhibitor; (b) a biguanide; and (c) an SGLT2 inhibitor is about 70% of the lowest diabetes therapeutic dose (LDTD) for each of (a) and (b), and about 50% of the lowest diabetes therapeutic dose (LDTD) for (c).

In some embodiments, the lowest diabetes therapeutic dose (LDTD) and the corresponding proposed dose and proposed dose range for the following compounds are as described in Table 5.

TABLE 5

| Agent | Lowest Diabetes Therapeutic Dose (LDTD) (mg) | Proposed Dose (mg) (% LDTD) | Proposed Dose Range (% LDTD) (mg) |
|---|---|---|---|
| sitagliptin | 25 | 17.5 (70) | 16.25-18.75 (65-75) |
| vildagliptin | 50 | 35 (70) | 32.5-37.5 (65-75) |
| saxagliptin | 2.5 | 1.75 (70) | 1.625-1.875 (65-75) |
| linagliptin | 5.0 | 3.5 (70) | 3.25-3.75 (65-75) |
| alogliptin | 6.25 | 4.375 (70) | 4.0625-4.6875 (65-75) |
| metformin | 500 | 350 (70) | 325-375 (65-75) |
| dapagliflozin | 5.0 | 2.5 (50) | 2.25-2.75 (45-55) |
| empagliflozin | 10.0 | 5.0 (50) | 4.5-5.5 (45-55) |
| canagliflozin | 100 | 50 (50) | 45-55 (45-55) |
| ertugliflozin | 5.0 | 2.5 (50) | 2.25-2.75 (45-55) |

In some embodiments, the pharmaceutical composition comprises: (a) sitagliptin as a DPP IV inhibitor; (b) metformin as a biguanide; and (c) dapagliflozin as an SGLT2 inhibitor. In some embodiments, the pharmaceutical composition comprises: (a) sitagliptin as a DPP IV inhibitor; (b) metformin as a biguanide; and (c) empagliflozin as an SGLT2 inhibitor. In some embodiments, the dose of sitagliptin is from about 1.625 mg to about 18.75 mg, the dose of metformin is from about 325 mg to about 375 mg, and the dose of dapagliflozin is from about 2.25 mg to about 2.75 mg.

In some embodiments, the dose of sitagliptin is from about 1.625 mg to about 18.75 mg and the dose of metformin is from about 325 mg to about 375 mg. In some embodiments, the dose of sitagliptin is from about 1.625 mg to about 18.75 mg and the dose of dapagliflozin is from about 2.25 mg to about 2.75 mg. In some embodiments, the dose of metformin is from about 325 mg to about 375 mg and the dose of dapagliflozin is from about 2.25 mg to about 2.75 mg.

In some embodiments, the dose of sitagliptin is from about 1.625 mg to about 18.75 mg, the dose of metformin is from about 325 mg to about 375 mg, and the dose of empagliflozin is from about 4.5 mg to about 5.5 mg.

In some embodiments, the dose of sitagliptin is from about 1.625 mg to about 18.75 mg and the dose of empagliflozin is from about 4.5 mg to about 5.5 mg. In some embodiments, the dose of metformin is from about 325 mg to about 375 mg and the dose of empagliflozin is from about 4.5 mg to about 5.5 mg.

In some embodiments, the dose of sitagliptin is about 17.5 mg, the dose of metformin is about 350 mg, and the dose of dapagliflozin is about 2.5 mg. In some embodiments, the dose of sitagliptin is about 17.5 mg and the dose of metformin is about 350 mg. In some embodiments, the dose of sitagliptin is about 17.5 mg and the dose of dapagliflozin is about 2.5 mg. In some embodiments, the dose of metformin is about 350 mg and the dose of dapagliflozin is about 2.5 mg.

In some embodiments, the dose of sitagliptin is about 17.5 mg, the dose of metformin is about 350 mg, and the dose of empagliflozin is about 5.0 mg. In some embodiments, the dose of sitagliptin is about 17.5 mg and the dose of metformin is about 350 mg. In some embodiments, the dose of sitagliptin is about 17.5 mg and the dose of empagliflozin is about 5.0 mg. In some embodiments, the dose of metformin is about 350 mg and the dose of empagliflozin is about 5.0 mg.

Formulations

In some embodiments, the DPP IV inhibitor, biguanide, and SGLT2 inhibitor are provided in one formulation. In some embodiments, the DPP IV inhibitor, biguanide, and SGLT2 inhibitor are each provided in a separate formulation. In some embodiments, two of the DPP IV inhibitor, biguanide, and SGLT2 inhibitor are provided in one formulation. In some embodiments, the DPP IV inhibitor and biguanide are provided in one formulation. In some embodiments, the DPP IV inhibitor and SGLT2 inhibitor are provided in one formulation. In some embodiments, the biguanide and SGLT2 inhibitor are provided in one formulation. In some embodiments, the pharmaceutical composition is in the form of a pill, a tablet, or a capsule. In some embodiments, the pharmaceutical composition is in the form of a pill. In some embodiments, the pharmaceutical composition is in the form of a tablet. In some embodiments, the pharmaceutical composition is in the form of a capsule. In some embodiments, the pharmaceutical composition is suitable for oral administration.

Other suitable formulations include, but are not limited to, those suitable for rectal, topical, buccal, parenteral (e.g., subcutaneous, intramuscular, intradermal, or intravenous), vaginal, or aerosol administration, although the most suitable form of administration in any given case will depend on the degree and severity of the condition being treated and on the nature of the particular compound being used. For example, disclosed compositions may be formulated as a unit dose.

Exemplary pharmaceutical compositions may be used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. In some embodiments, capsules are prepared by encapsulating tablets in hard-gelatin capsules (e.g., over-encapsulation). Tablets, and other solid dosage forms, such as dragees, capsules, pills and granules, may optionally be scored or prepared with coatings and shells, such as enteric coatings and other coatings well known in the pharmaceutical-formulating art.

Methods of Treatment

The pharmaceutical compositions described herein are useful for treating a metabolic disorder in a subject in need thereof. The pharmaceutical compositions described herein are useful for treating diabetes in a subject in need thereof.

The high incidence of therapeutic failure is a major contributor to the high rate of long-term hyperglycemia-associated complications or chronic damages (including microvascular complications such as diabetic nephropathy, retinopathy or neuropathy, and macrovascular complications such as coronary heart disease, cerebrovascular disease, and peripheral vascular disease) in patients with type 2 diabetes. Therefore, there is an unmet medical need for methods, medicaments, and pharmaceutical compositions with a good efficacy with regard to glycemic control, with regard to disease-modifying properties and with regard to reduction of cardiovascular morbidity and mortality while at the same time showing an improved safety profile.

In some embodiments, the treatment or methods of the present disclosure result in one or more of the following:
  i. preventing, slowing progression of, delaying, or treating a metabolic disorder;
  ii. preventing, slowing progression of, delaying, or treating diabetes;
  iii. improving glycemic control and/or for reducing of fasting plasma glucose, of postprandial plasma glucose, of continuously measured blood glucose, and/or of glycosylated hemoglobin HbA1c;
  iv. preventing, slowing, delaying or reversing progression from impaired glucose tolerance, impaired fasting blood glucose, and/or insulin resistance from metabolic syndrome and/or type 2 diabetes mellitus;
  v. preventing, slowing progression of, delaying or treating of a condition or disorder selected from the group consisting of vascular and non-vascular complications of diabetes mellitus;
  vi. preventing, slowing progression of, delaying, or treating impairment of renal function;
  vii. preventing, slowing progression of, delaying, or treating impaired renal function;
  viii. preventing, slowing progression of, delaying, or treating retinal vascular disease;
  ix. reducing body weight and/or body fat or preventing an increase in body weight and/or body fat or facilitating a reduction in body weight and/or body fat;
  x. preventing or treating the degeneration of pancreatic beta cells and/or for improving and/or restoring the functionality of pancreatic beta cells and/or restoring the functionality of pancreatic insulin secretion;
  xi. preventing, slowing, delaying or treating diseases or conditions attributed to an abnormal accumulation of ectopic fat;
  xii. maintaining and/or improving the insulin sensitivity and/or for treating or preventing hyperinsulinemia and/or insulin resistance,
  xiii. preventing, slowing progression of, delaying, or treating new onset diabetes after transplantation (NODAT) and/or post-transplant metabolic syndrome (PTMS);
  xiv. preventing, delaying, or reducing NODAT and/or PTMS associated complications including microvascular and macrovascular diseases and events, graft rejection, infection, and death;

xv. treating hyperuricemia and hyperuricemia associated conditions;
xvi. treating or preventing kidney stones; and/or
xvii. treating hyponatremia.

In some embodiments, the treatment results in slowing progression of, delaying or treating a metabolic disorder, in particular of type 2 diabetes mellitus.

In some embodiments, the treatment results in an improvement in glycemic control in a patient in need thereof, in particular in patients with type 2 diabetes mellitus.

In some embodiments, the treatment results in an improvement in glycemic control in a patient with insufficient glycemic control despite monotherapy with an antidiabetic drug or despite combination therapy with two antidiabetic drugs.

In some embodiments, the treatment results in slowing or delaying progression from impaired glucose tolerance (IGT), impaired fasting blood glucose (IFG), insulin resistance and/or metabolic syndrome to type 2 diabetes mellitus.

In some embodiments, the method results in prevention, slowing progression of, delaying or treatment of a condition or disorder from the group consisting of complications of diabetes mellitus.

In some embodiments, the treatment results in a reduction in the weight or prevention of an increase of the weight in a patient in need thereof.

In some embodiments, the method results in efficacious treatment of metabolic disorders, such as diabetes mellitus, impaired glucose tolerance (IGT), impaired fasting blood glucose (IFG), and/or hyperglycemia, with good pharmacological and/or pharmacokinetic and/or physicochemical properties.

In some embodiments, the method results in efficacious treatment of metabolic disorders, such as diabetes mellitus, impaired glucose tolerance (IGT), impaired fasting blood glucose (IFG), and/or hyperglycemia, with greater long term tolerability and reduced risk of side effects (e.g., low blood sugar, pancreatic cancer, hypersensitivity reactions including anaphylaxis, angioedema, rash, urticaria, cutaneous vasculitis, and exfoliative skin conditions including Stevens-Johnson syndrome; hepatic enzyme elevations; acute pancreatitis, including fatal and nonfatal hemorrhagic and necrotizing pancreatitis; worsening renal function, including acute renal failure (sometimes requiring dialysis); severe and disabling arthralgia; constipation; vomiting; headache; myalgia; pain in extremity; back pain; pruritus; and/or pemphigoid, joint pain, lactic acidosis, vitamin B12 and folic acid deficiency, nasopharyngitis, upper respiratory tract infection).

In some embodiments, treatment results in improved treatment of diabetes that is greater than the treatment obtained with the full lowest diabetic therapeutic dose of any one of the DPP IV inhibitor, the biguanide, and the SGLT2 inhibitor in the pharmaceutical composition.

In some embodiments, treatment results in improved treatment of diabetes that is greater than the treatment obtained with the full lowest diabetic therapeutic dose of the DPP IV inhibitor in the pharmaceutical composition. In some embodiments, treatment results in improved treatment of diabetes that is greater than the treatment obtained with the full lowest diabetic therapeutic dose of the biguanide in the pharmaceutical composition. In some embodiments, treatment results in improved treatment of diabetes that is greater than the treatment obtained with the full lowest diabetic therapeutic dose of the SGLT2 inhibitor in the pharmaceutical composition.

In some embodiments, treatment results in greater long term tolerability and reduced risk of side effects when compared to treatment with the full lowest diabetic therapeutic dose of any one of the DPP IV inhibitor, the biguanide, and the SGLT2 inhibitor in the pharmaceutical composition. In some embodiments, the treatment results in greater long term tolerability and reduced risk of side effects when compared to treatment with the full lowest diabetic therapeutic dose of the DPP IV inhibitor in the pharmaceutical composition. In some embodiments, the treatment results in greater long term tolerability and reduced risk of side effects when compared to treatment with the full lowest diabetic therapeutic dose of the biguanide in the pharmaceutical composition. In some embodiments, the treatment results in greater long term tolerability and reduced risk of side effects when compared to treatment with the full lowest diabetic therapeutic dose of the SGLT2 inhibitor in the pharmaceutical composition.

In some embodiments, treatment results in an improvement in diabetes and/or associated conditions that is greater than or equal to the improvement obtained with the combination of any two of the DPP IV inhibitor, the biguanide, and the SGLT2 inhibitor in the pharmaceutical composition. In some embodiments, treatment results in an improvement in diabetes and/or associated conditions that is greater than or equal to the improvement obtained with a combination of any two of the DPP IV inhibitor, the biguanide, and the SGLT2 inhibitor in the pharmaceutical composition, wherein the dose of each the DPP IV inhibitor, the biguanide, and the SGLT2 inhibitor is about 25% of the lowest diabetic therapeutic dose. In some embodiments, treatment results in an improvement in diabetes and/or associated conditions that is greater than or equal to the improvement obtained with a combination of any two of the DPP IV inhibitor, the biguanide, and the SGLT2 inhibitor in the pharmaceutical composition, wherein the dose of each the DPP IV inhibitor, the biguanide, and the SGLT2 inhibitor is about 33% of the lowest diabetic therapeutic dose. In some embodiments, treatment results in an improvement in diabetes and/or associated conditions that is greater than or equal to the improvement obtained with a combination of any two of the DPP IV inhibitor, the biguanide, and the SGLT2 inhibitor in the pharmaceutical composition, wherein the dose of each the DPP IV inhibitor, the biguanide, and the SGLT2 inhibitor is about 50% of the lowest diabetic therapeutic dose. In some embodiments, treatment results in an improvement in diabetes and/or associated conditions that is greater than or equal to the improvement obtained with a combination of any two of the DPP IV inhibitor, the biguanide, and the SGLT2 inhibitor in the pharmaceutical composition, wherein the dose of each the DPP IV inhibitor, the biguanide, and the SGLT2 inhibitor is about 70% of the lowest diabetic therapeutic dose. In some embodiments, treatment results in an improvement in diabetes and/or associated conditions that is greater than or equal to the improvement obtained with a combination of any two of the DPP IV inhibitor, the biguanide, and the SGLT2 inhibitor in the pharmaceutical composition, wherein the dose of the DPP IV inhibitor and the biguanide are about 70% of the lowest diabetic therapeutic dose for each of the DPP IV inhibitor and the biguanide, and the dose of the SGLT2 inhibitor is about 50% of the lowest diabetic therapeutic dose for the SGLT2 inhibitor.

In some embodiments, the treatment results in greater long term tolerability and reduced risk of side effects when compared to treatment with a combination of any two of the DPP IV inhibitor, the biguanide, and the SGLT2 inhibitor in the pharmaceutical composition, wherein the dose of each the DPP IV inhibitor, the biguanide, and the SGLT2 inhibitor is about 50% of the lowest diabetic therapeutic dose.

In some embodiments, the treatment is the initial or first-line treatment of diabetes. In some embodiments, the subject has a very mild elevation of blood sugar prior to treatment. In some embodiments, the subject is not on any previous diabetic therapy prior to treatment. In some embodiments, the subject has a very mild elevation of blood sugar prior to treatment and is not on any previous diabetic therapy prior to treatment. In some embodiments, the subject has persisting elevation of blood sugar after treatment with one or two of a DPP IV inhibitor, a biguanide, or a SGLT2 inhibitor at the LDTD or higher dose.

This present disclosure recognizes that the use of the DPP IV inhibitor in the pharmaceutical compositions disclosed herein in some embodiments provides beneficial therapeutic effects, which include, but are not limited to, significant reduction in blood sugar, significant reduction in blood sugar among subjects with mild elevation in blood sugar, greater long term tolerability, and reduced risk of side effects.

It is also recognized herein that in some embodiments, the triple low-dose combination formulation described herein comprising a DPP IV inhibitor, a biguanide, and an SGLT2 inhibitor provides reductions in blood sugar greater than the LDTD of each individual drug given singly. For example, in some embodiments, a triple combination formulation comprising 70% DPP IV inhibitor, 50% biguanide, and 70% SGLT2 inhibitor provides reductions in blood sugar greater than, or substantially greater than, the LDTD of the DPP IV inhibitor, or the LDTD of biguanide, or the LDTD of the SGLT2 inhibitor, given singly. As another example, in some embodiments, a triple combination formulation comprising 50% DPP IV inhibitor, 50% biguanide, and 50% SGLT2 inhibitor provides reductions in blood sugar greater than, or substantially greater than, the LDTD of the DPP IV inhibitor, or the LDTD of biguanide or the LDTD of the SGLT2 inhibitor, given singly.

It is also recognized herein that in some embodiments, the triple low-dose combination formulation described herein comprising a DPP IV inhibitor, a biguanide, and an SGLT2 inhibitor provides reductions in blood sugar greater than twice the LDTD of each individual drug given singly. For example, in some embodiments, a triple combination formulation comprising 70% DPP IV inhibitor, 50% biguanide, and 70% SGLT2 inhibitor provides reductions in blood sugar greater than, or substantially greater than twice the LDTD of each individual drug given singly. As another example, in some embodiments, a triple combination formulation comprising 50% DPP IV inhibitor, 50% biguanide, and 50% SGLT2 inhibitor provides reductions in blood sugar greater than, or substantially greater than twice the LDTD of each individual drug given singly.

Additional Embodiments

Embodiments includes embodiment 1 to 92 following.

Embodiment 1

A pharmaceutical composition comprising:
a) a dipeptidyl peptidase IV (DPP IV) inhibitor;
b) a biguanide; and
c) a subtype 2 sodium-glucose transport protein (SGLT2) inhibitor;
wherein (a), (b), and (c) are each at about 20-75% of the lowest diabetes therapeutic dose (LDTD).

Embodiment 2

The pharmaceutical composition of Embodiment 1, wherein the DPP IV inhibitor is a gliptin.

Embodiment 3

The pharmaceutical composition of Embodiment 1 or 2, wherein the DPP-IV inhibitor is sitagliptin, vildagliptin, saxagliptin, linagliptin, gemigliptin, anagliptin, teneligliptin, alogliptin, trelagliptin, omarigliptin, evogliptin, gosogliptin, dutogliptin, or the pharmaceutically acceptable salt or hydrate thereof.

Embodiment 4

The pharmaceutical composition of any one of Embodiments 1-3, wherein the DPP IV inhibitor is sitagliptin or the pharmaceutically acceptable salt thereof.

Embodiment 5

The pharmaceutical composition of Embodiment 4, wherein the DPP IV inhibitor is sitagliptin phosphate.

Embodiment 6

The pharmaceutical composition of any one of Embodiments 1-5, wherein the biguanide is metformin or the pharmaceutically acceptable salt or hydrate thereof.

Embodiment 7

The pharmaceutical composition of Embodiment 6, wherein the biguanide is metformin hydrochloride.

Embodiment 8

The pharmaceutical composition of Embodiment 6 or 7, wherein the metformin is formulated for immediate release.

Embodiment 9

The pharmaceutical composition of Embodiment 6 or 7, wherein the metformin is formulated for slow release.

Embodiment 10

The pharmaceutical composition of any one of Embodiments 1-9, wherein the SGLT2 inhibitor is a gliflozin.

Embodiment 11

The pharmaceutical composition of Embodiment 10, wherein the SGLT2 inhibitor is dapagliflozin, empagliflozin, canagliflozin, ipragliflozin (ASP-1941), tofogliflozin, remogliflozin, sergliflozin, ertugliflozin, sotagliflozin, or the pharmaceutically acceptable salt, hydrate, or combinations thereof.

Embodiment 12

The pharmaceutical composition of Embodiment 11, wherein the SGLT2 inhibitor is dapagliflozin or pharmaceutically acceptable salt, hydrate, or a combination thereof.

Embodiment 13

The pharmaceutical composition of Embodiment 12, wherein the SGLT2 inhibitor is a dapagliflozin hydrate.

Embodiment 14

The pharmaceutical composition of Embodiment 13, wherein the SGLT2 inhibitor is dapagliflozin propanediol monohydrate.

Embodiment 15

The pharmaceutical composition of any one of Embodiments 1-14, wherein the dose of each (a), (b), and (c) is from about 40% to about 75% of the lowest diabetes therapeutic dose (LDTD).

Embodiment 16

The pharmaceutical composition of any one of Embodiments 1-14, wherein the dose of each (a), (b), and (c) is from about 60% to about 75% of the lowest diabetes therapeutic dose (LDTD).

Embodiment 17

The pharmaceutical composition of any one of Embodiments 1-14, wherein the dose of each (a), (b), and (c) is from about 65% to about 75% of the lowest diabetes therapeutic dose (LDTD).

Embodiment 18

The pharmaceutical composition of any one of Embodiments 1-14, wherein the dose of each (a), (b), and (c) is from about 40% to about 70% of the lowest diabetes therapeutic dose (LDTD).

Embodiment 19

The pharmaceutical composition of any one of Embodiments 1-14, wherein the dose of each (a), (b), and (c) is from about 40% to about 60% of the lowest diabetes therapeutic dose (LDTD).

Embodiment 20

The pharmaceutical composition of any one of Embodiments 1-14, wherein the dose of each (a), (b), and (c) is from about 45% to about 55% of the lowest diabetes therapeutic dose (LDTD).

Embodiment 21

The pharmaceutical composition of any one of Embodiments 1-18, wherein the DPP IV inhibitor is about 70% of the lowest diabetes therapeutic dose (LDTD) for the DPP IV inhibitor.

Embodiment 22

The pharmaceutical composition of Embodiment 18, wherein the DPP IV inhibitor is sitagliptin, and the dose of sitagliptin is about 17.5 mg.

Embodiment 23

The pharmaceutical composition of any one of Embodiments 1-15 or 18-20, wherein the DPP IV inhibitor is about 50% of the lowest diabetes therapeutic dose (LDTD) for the DPP IV inhibitor.

Embodiment 24

The pharmaceutical composition of Embodiment 23, wherein the DPP IV inhibitor is sitagliptin, and the dose of sitagliptin is about 12.5 mg.

Embodiment 25

The pharmaceutical composition of any one of Embodiments 1-18, wherein the biguanide is about 70% of the lowest diabetes therapeutic dose (LDTD) for the biguanide.

Embodiment 26

The pharmaceutical composition of Embodiment 25, wherein the biguanide is metformin hydrochloride, and the dose of metformin hydrochloride is about 350 mg.

Embodiment 27

The pharmaceutical composition of any one of Embodiments 1-15 or 18-24, wherein the biguanide is about 50% of the lowest diabetes therapeutic dose (LDTD) for the biguanide.

Embodiment 28

The pharmaceutical composition of Embodiment 27, wherein the biguanide is metformin hydrochloride, and the dose of metformin hydrochloride is about 250 mg.

Embodiment 29

The pharmaceutical composition of any one of Embodiments 1-15 or 18-28, wherein the SGLT2 inhibitor is about 50% of the lowest diabetes therapeutic dose (LDTD) for the SGLT2 inhibitor.

Embodiment 30

The pharmaceutical composition of Embodiment 29, wherein the SGLT2 inhibitor is dapagliflozin, and the dose of dapagliflozin is about 2.5 mg.

Embodiment 31

The pharmaceutical composition of Embodiment 1, wherein the DPP IV inhibitor is sitagliptin, the biguanide is metformin, and the SGLT2 inhibitor is dapagliflozin or empagliflozin.

Embodiment 32

The pharmaceutical composition of Embodiment 31, wherein the dose of sitagliptin is from about 5.0 mg to about 18.75 mg, the dose of metformin is from about 100 mg to about 375 mg, and the dose of dapagliflozin is from about 1.0 mg to about 3.75 mg.

Embodiment 33

The pharmaceutical composition of Embodiment 31, wherein the dose of sitagliptin is from about 5.0 mg to about 18.75 mg, the dose of metformin is from about 100 mg to about 375 mg, and the dose of empagliflozin is from about 2.0 mg to about 7.5 mg.

Embodiment 34

The pharmaceutical composition of Embodiment 31, wherein the dose of sitagliptin is from about 10 mg to about 16.25 mg, the dose of metformin is from about 200 mg to about 325 mg, and the dose of dapagliflozin is from about 2.0 mg to about 3.25 mg.

Embodiment 35

The pharmaceutical composition of Embodiment 31, wherein the dose of sitagliptin is from about 10 mg to about 15 mg, the dose of metformin is from about 200 mg to about 300 mg, and the dose of dapagliflozin is from about 2 mg to about 3 mg.

Embodiment 36

The pharmaceutical composition of Embodiment 31, wherein the dose of sitagliptin is from about 11.25 mg to about 13.75 mg, the dose of metformin is from about 225 mg to about 275 mg, and the dose of dapagliflozin is from about 2.25 mg to about 2.75 mg.

Embodiment 37

The pharmaceutical composition of Embodiment 31, wherein the dose of sitagliptin is about 12.5 mg, the dose of metformin is about 250 mg, and the dose of dapagliflozin is about 2.5 mg.

Embodiment 38

The pharmaceutical composition of any one of Embodiments 1-11, wherein the dose of each (a), (b), and (c) is from about 30% to about 40% of the lowest diabetes therapeutic dose (LDTD).

Embodiment 39

The pharmaceutical composition of any one of Embodiments 1-11, wherein the dose of each (a), (b), and (c) is from about 30% to about 35% of the lowest diabetes therapeutic dose (LDTD).

Embodiment 40

The pharmaceutical composition of Embodiment 38 or 39, wherein the SGLT2 inhibitor is about 33% of the lowest diabetes therapeutic dose (LDTD) for the SGLT2 inhibitor.

Embodiment 41

The pharmaceutical composition of Embodiment 40, wherein the SGLT2 inhibitor is dapagliflozin, and the dose of dapagliflozin is about 1.65 mg.

Embodiment 42

The pharmaceutical composition of Embodiment 40, wherein the SGLT2 inhibitor is empagliflozin, and the dose of empagliflozin is about 3.3 mg.

Embodiment 43

The pharmaceutical composition of Embodiment 38, wherein the DPP IV inhibitor is sitagliptin, the biguanide is metformin, and the SGLT2 inhibitor is dapagliflozin or empagliflozin.

Embodiment 44

The pharmaceutical composition of Embodiment 43, wherein the dose of sitagliptin is from about 7.5 mg to about 10 mg and the dose of metformin is from about 150 mg to about 200 mg.

Embodiment 45

The pharmaceutical composition of Embodiment 44, wherein the SGLT2 inhibitor is dapagliflozin and the dose of dapagliflozin is from about 1.5 mg to about 2.0 mg.

Embodiment 46

The pharmaceutical composition of Embodiment 44, wherein the SGLT2 inhibitor is empagliflozin and the dose of empagliflozin is from about 3.0 mg to about 4.0 mg.

Embodiment 47

The pharmaceutical composition of Embodiment 40, wherein the dose of sitagliptin is about 8.25 mg and the dose of metformin is about 165 mg.

Embodiment 48

The pharmaceutical composition of Embodiment 44, wherein the SGLT2 inhibitor is dapagliflozin and the dose of dapagliflozin is about 1.65 mg.

Embodiment 49

The pharmaceutical composition of Embodiment 44, wherein the SGLT2 inhibitor is empagliflozin, and the dose of empagliflozin is about 3.3 mg.

Embodiment 50

The pharmaceutical composition of any one of Embodiments 1-11, wherein the dose of each (a), (b), and (c) is from about 20% to about 30% of the lowest diabetes therapeutic dose (LDTD).

Embodiment 51

The pharmaceutical composition of any one of Embodiments 1-11, wherein the dose of each (a), (b), and (c) is from about 22% to about 28% of the lowest diabetes therapeutic dose (LDTD).

Embodiment 52

The pharmaceutical composition of Embodiment 50 or 51, wherein the dose of the SGLT2 inhibitor is about 25% of the lowest diabetes therapeutic dose (LDTD) for the SGLT2 inhibitor.

Embodiment 53

The pharmaceutical composition of Embodiment 52, wherein the SGLT2 inhibitor is dapagliflozin, and the dose of dapagliflozin is about 1.25 mg.

Embodiment 54

The pharmaceutical composition of Embodiment 52, wherein the SGLT2 inhibitor is empagliflozin, and the dose of empagliflozin is about 2.5 mg.

Embodiment 55

The pharmaceutical composition of Embodiment 51, wherein the DPP IV inhibitor is sitagliptin, the biguanide is metformin, and the SGLT2 inhibitor is dapagliflozin or empagliflozin.

Embodiment 56

The pharmaceutical composition of Embodiment 55, wherein the dose of sitagliptin is from about 5 mg to about 7.5 mg and the dose of metformin is from about 100 mg to about 150 mg.

Embodiment 57

The pharmaceutical composition of Embodiment 56, wherein the SGLT2 inhibitor is dapagliflozin, and the dose of dapagliflozin is about 1.0 mg.

Embodiment 58

The pharmaceutical composition of Embodiment 56, wherein the SGLT2 inhibitor is empagliflozin, and the dose of empagliflozin is about 2.0 mg.

Embodiment 59

The pharmaceutical composition of Embodiment 55, wherein the dose of sitagliptin is about 6.25 mg and the dose of metformin is about 150 mg.

Embodiment 60

The pharmaceutical composition of Embodiment 59, wherein the SGLT2 inhibitor is dapagliflozin, and the dose of dapagliflozin is about 1.5 mg.

Embodiment 61

The pharmaceutical composition of Embodiment 59, wherein the SGLT2 inhibitor is empagliflozin, and the dose of empagliflozin is about 3.0 mg.

Embodiment 62

The pharmaceutical composition of any one of Embodiments 1-61, wherein (a), (b), and (c) are provided in one formulation.

Embodiment 63

The pharmaceutical composition of any one of Embodiments 1-61, wherein (a), (b), and (c) are each provided in a separate formulation.

Embodiment 64

The pharmaceutical composition of any one of Embodiments 1-61, wherein two of the (a), (b), and (c) are provided in one formulation.

Embodiment 65

The pharmaceutical composition of any one of Embodiments 1-64, wherein the pharmaceutical composition is suitable for oral administration.

Embodiment 66

The pharmaceutical composition of any one of Embodiments 1-65, wherein the pharmaceutical composition is in the form of pill, tablet or capsule.

Embodiment 67

A pharmaceutical composition comprising:
a) a dipeptidyl peptidase IV (DPP IV) inhibitor;
b) a biguanide; and
c) a subtype 2 sodium-glucose transport protein (SGLT2) inhibitor;
wherein (a) and (b) are each at about 65%-75% of the lowest diabetes therapeutic dose (LDTD), and (c) is at about 45%-55% of the lowest diabetes therapeutic dose (LDTD).

Embodiment 68

The pharmaceutical composition of Embodiment 67, wherein the DPP IV inhibitor is sitagliptin and the dose of sitagliptin is from about 16.25 mg to about 18.75 mg.

Embodiment 69

The pharmaceutical composition of Embodiment 67, wherein the biguanide is metformin and the dose of metformin is from about 325 mg to about 375 mg.

Embodiment 70

The pharmaceutical composition of Embodiment 67, wherein the SGLT2 inhibitor is dapagliflozin, and the dose of dapagliflozin from about 2.25 mg to about 2.75 mg.

Embodiment 71

The pharmaceutical composition of Embodiment 67, wherein the SGLT2 inhibitor is empagliflozin, and the dose of empagliflozin from about 4.5 mg to about 7.5 mg.

Embodiment 72

The pharmaceutical composition of Embodiment 67, wherein the DPP IV inhibitor is at about 70% of the lowest diabetes therapeutic dose (LDTD) for the DPP IV inhibitor.

Embodiment 73

The pharmaceutical composition of Embodiment 67 or 71, wherein the biguanide is at about 70% of the lowest diabetes therapeutic dose (LDTD) for the biguanide.

Embodiment 74

The pharmaceutical composition of any one of Embodiments 67 or 72-73, wherein the SGLT2 inhibitor is at about 50% of the lowest diabetes therapeutic dose (LDTD) for the SGLT2 inhibitor.

Embodiment 75

The pharmaceutical composition of any one of Embodiments 67 or 72-74, wherein the DPP IV inhibitor is sitagliptin, the biguanide is metformin, and the SGLT2 inhibitor is dapagliflozin or empagliflozin.

Embodiment 76

The pharmaceutical composition of Embodiment 75, wherein the dose of sitagliptin is about 17.5 mg, the dose of metformin is about 350 mg, and the dose of dapagliflozin is about 2.5 mg.

Embodiment 77

The pharmaceutical composition of Embodiment 75, wherein the dose of sitagliptin is about 17.5 mg, the dose of metformin is about 350 mg, and the dose of empagliflozin is about 5.0 mg.

Embodiment 78

The pharmaceutical composition of any one of Embodiments 67 or 72-74, wherein the DPP IV inhibitor is sitagliptin and the dose of the sitagliptin is about 17.5 mg.

Embodiment 79

The pharmaceutical composition of any one of Embodiments 67 or 72-74, wherein the biguanide is metformin and the dose of the metformin is about 350 mg.

Embodiment 80

The pharmaceutical composition of any one of Embodiments 67 or 72-74, wherein the SGLT2 inhibitor is dapagliflozin and the dose of the dapagliflozin is about 2.5 mg.

Embodiment 81

The pharmaceutical composition of any one of Embodiments 67 or 72-74, wherein the SGLT2 inhibitor is empagliflozin and the dose of the empagliflozin is about 5.0 mg.

Embodiment 82

The pharmaceutical composition of any one of Embodiments 67-82, wherein (a), (b), and (c) are provided in one formulation.

Embodiment 83

The pharmaceutical composition of any one of Embodiments 67-82, wherein (a), (b), and (c) are each provided in a separate formulation.

Embodiment 84

The pharmaceutical composition of any one of Embodiments 67-82, wherein two of the (a), (b), and (c) are provided in one formulation.

Embodiment 85

The pharmaceutical composition of any one of Embodiments 67-84, wherein the pharmaceutical composition is suitable for oral administration.

Embodiment 86

The pharmaceutical composition of any one of Embodiments 67-85, wherein the pharmaceutical composition is in the form of pill, tablet or capsule.

Embodiment 87

The pharmaceutical composition of any one of Embodiments 67-86, wherein the metformin is formulated for immediate release.

Embodiment 88

The pharmaceutical composition of any one of Embodiments 67-86, wherein the metformin is formulated for slow release.

Embodiment 89

A method of treating diabetes in a subject in need thereof comprising administering the pharmaceutical composition of any one of Embodiments 1-88.

Embodiment 90

The method of Embodiment 89, wherein the subject has persisting elevation of blood sugar after treatment with one or two of a DPP IV inhibitor, a biguanide, or an SGLT2 inhibitor at the LDTD or higher dose.

Embodiment 91

The method of Embodiment 89, wherein the administration of the pharmaceutical composition is an initial or first-line treatment of diabetes.

Embodiment 92

A method of improving, slowing the progression of, or delaying a metabolic disorder such as diabetes mellitus, impaired glucose tolerance, impaired fasting blood glucose, hyperglycemia, postprandial hyperglycemia, overweight, obesity, metabolic syndrome, impaired renal function, gestational diabetes, new onset diabetes after transplantation (NODAT) and complications associated therewith, and post-transplant metabolic syndrome (PTMS) and complications associated therewith, comprising administering to a subject in need thereof the pharmaceutical composition of any one of Embodiments 1-88.

The disclosure will be further understood by the following non-limiting examples.

EXAMPLES

The examples set forth below are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims.

Example 1: Study of the Effects of a Combination of a DPP IV Inhibitor, a Biguanide, and an SGLT2 Inhibitor on Whole Blood Glucose (WBG), Glycated Haemoglobin (HbA1c), Insulin, and Creatinine Levels Study Design:
Zucker rat model of diet induced diabetes (Zucker Diabetic Fatty Rats)
Parallel randomized study
10 animals in each of 4 treatment groups
21 days of treatment
Main Study Outcomes:
Glucose (measured at multiple time points before and during treatment)
HbA1c (before and at the end of the treatment period)
Insulin (before and at the end of the treatment period)
Creatinine (before and at the end of the treatment period)

TABLE 6

Treatment groups and doses in ultra low-dose glucose-lowering drug combinations

| Group | Test Article | | Human Dose Level (mg) | Animal Dose Level (mg/kg) | Animal Concentration (mg/mL) | Animal Volume (mL/kg) |
|---|---|---|---|---|---|---|
| 1 | Vehicle | Metformin | 0 | 0 | 0 | 10 |
| 2 | | Sitagliptin | 17.5 | 1.545 | 0.1545 | |
| | Composition A | Dapagliflozin | 2.5 | 0.220 | 0.0220 | 10 |
| | | Metformin | 350 | 30.833 | 3.0833 | |
| 3 | Composition B | Sitagliptin | 17.5 | 1.545 | 0.1545 | |
| | | Empagliflozin | 5.0 | 0.440 | 0.0440 | 10 |
| | | Metformin | 350 | 30.833 | 3.0833 | |
| 4 | 1K-MET | Metformin | 1000 | 88.095 | 8.8095 | 10 |

Ten Zucker Diabetic Fatty (ZDF) rats were randomly allocated to each of the four different treatment groups (Table 6). Whole blood glucose measurements were made from 4 days before dosing, then daily until for 8 days, then at reduced frequency. Measurements of HbA1c and creatinine were made the day prior to dosing, then at days 9 and 21. Insulin measurements were made the day prior to dosing then on day 20. A clinical chemistry sample from one animal in the vehicle group on day 9 was not available so there is a missing measurement for creatinine and HbA1c on that day Methods
Statistical Analysis Whole blood glucose, HbA1c and Creatinine were each analyzed using a linear mixed mode (proc mixed in SAS/STAT 14.2). For WBC, unstructured, autoregressive, exchangeable and Toeplitz correlation structures for repeated measurements across the study were compared using Akaike Information Criterion and Bayesian Information Criterion. The Toeplitz correlation structure was selected as the best fitting structure. For HbA1c and Creatinine an exchangeable structure was used as there were only two measurements. Denominator degrees of freedom were calculated using the between-within subject method. The model included coefficients for baseline measurement (the closest measurement preceding dosing), type of drug treatment, time and an interaction between drug treatment and time. Marginal means (with 95% confidence intervals) for the measurement at each period for each drug were estimated, and an overall marginal mean (with 95% confidence interval) for measurements across time was estimated using weights that reflect the differing amounts of time in each measurement period (assuming each measurement represented all time since the preceding measurement). A likelihood ratio test of overall differences between treatment was initially used, if significant (p<0.05) then we tested for differences between each combination of treatments.

For Insulin, a baseline measure and a measurement at day 20 was available, so the ANCOVA approach (linear regression with the baseline value as a covariate) was used to test for differences in this measurement between treatments. The interaction between baseline value and treatment was tested but there was no evidence of an interaction, therefore the main effects were retained.

To test for robustness of the linear mixed model and ANCOVA models a bootstrapped 95% CI (percentile method) for the weighted marginal mean of measurements across the entire study period or single outcome measurement using 2000 replicates was estimated. The bootstrap sampling was done on individual animal (using complete measurements), with stratification by treatment type.

Results

It was found that there is an overall difference among treatments for the primary outcome WBG (p<0.001, Table 7), and the secondary outcomes of HbA1c (p<0.0001, Table 8), Insulin (p<0.0001, Table 9), and Serum Creatinine (p<0.0001, Table 10).

TABLE 7

Number of available measurements for analysis by outcome, timing, and treatment

| Outcome | Days from dosing | Vehicle | Composition A | Composition B | 1K-MET |
|---|---|---|---|---|---|
| Serum Creatinine | 9 | 9 | 10 | 10 | 10 |
| | 21 | 10 | 10 | 10 | 10 |
| Whole Blood Glucose | 1 | 10 | 10 | 10 | 10 |
| | 2 | 10 | 10 | 10 | 10 |
| | 3 | 10 | 10 | 10 | 10 |
| | 4 | 10 | 10 | 10 | 10 |
| | 5 | 10 | 10 | 10 | 10 |
| | 6 | 10 | 10 | 10 | 10 |
| | 7 | 10 | 10 | 10 | 10 |
| | 8 | 10 | 10 | 10 | 10 |
| | 12 | 10 | 10 | 10 | 10 |

TABLE 7-continued

Number of available measurements for analysis by outcome, timing, and treatment

| Outcome | Days from dosing | Vehicle | Composition A | Composition B | 1K-MET |
|---|---|---|---|---|---|
| | 14 | 10 | 10 | 10 | 10 |
| | 16 | 10 | 10 | 10 | 10 |
| | 19 | 10 | 10 | 10 | 10 |
| | 21 | 10 | 10 | 10 | 10 |
| HbA1c | 9 | 9 | 10 | 10 | 10 |
| | 21 | 10 | 10 | 10 | 10 |
| Insulin | 20 | 10 | 10 | 10 | 10 |

TABLE 8

Effects of combinations of glucose lowering medications on whole blood glucose (mg/dL)

| Comparison | Level | Estimate (95% CI) | P-value |
|---|---|---|---|
| Overall difference between treatments | | | <.0001 |
| Overall level in WBG after dosing (95% CI) | Vehicle | 418.3 (397.4-439.2) | |
| | Composition A | 213.2 (192.3-234.0) | |
| | Composition B | 371.5 (350.7-392.4) | |
| | 1K-MET | 442.7 (421.8-463.5) | |
| Pairwise comparisons | Vehicle vs Composition A | −205.2 (−234.7−−175.6) | <.0001 |
| | Vehicle vs Composition B | −46.8 (−76.3−−17.3) | 0.0026 |
| | Vehicle vs 1K-MET | 24.4 (−5.2-53.9) | 0.1035 |
| | Composition A vs 1K-MET | 229.5 (200.0-259.0) | <.0001 |
| | Composition B vs Composition A | −158.4 (−187.9−−128.9) | <.0001 |
| | Composition B vs 1K-MET | 71.1 (41.6-100.7) | <.0001 |

TABLE 9

Effects of combinations of glucose lowering medications on HbA1c (%)

| Comparison | Level | Estimate (95% CI) | P-value |
|---|---|---|---|
| Overall difference between treatments | | | <.0001 |
| Overall level in WBG after dosing (95% CI) | Vehicle | 6.86 (6.63-7.10) | |
| | Composition A | 4.75 (4.53-4.98) | |
| | Composition B | 5.83 (5.61-6.06) | |
| | 1K-MET | 6.52 (6.29-6.75) | |
| Pairwise comparisons | Vehicle vs Composition A | −2.11 (−2.44−−1.78) | <.0001 |
| | Vehicle vs Composition B | −1.03 (−1.36−−0.70) | <.0001 |
| | Vehicle vs 1K-MET | −0.35 (−0.68−−0.01) | 0.0410 |
| | Composition A vs 1K-MET | 1.76 (1.44-2.08) | <.0001 |
| | Composition B vs Composition A | −1.08 (−1.40−−0.76) | <.0001 |
| | Composition B vs 1K-MET | 0.68 (0.36-1.00) | 0.0001 |

For WBG, Composition A ($p<0.0001$) and Composition B ($p=0.0026$) groups were significantly lower across the post-dose measurement period. Composition A lowered WBG by 205 mg/dL relative to the vehicle, and Composition B lowered WBG by 47 mg/dL relative to the vehicle. There was significant interaction between time and treatment ($p<0.0001$), with WBG increasing by small amount in most of the treatments except for Composition B (FIG. 1). GMR-4b had a similar WBG to other treatments immediately after dosing (day 1), but then declined and stayed lower for the remainder of the study period.

Figure 2:
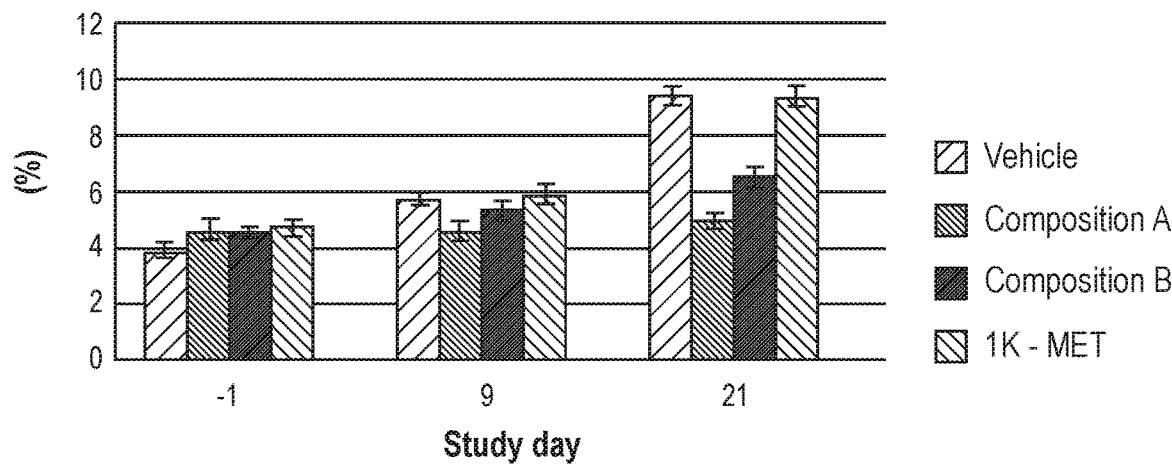
FIG. 2 shows Hemoglobin A1c (%) post-dosing by treatment group. Error bars represent standard error of the mean (SEM).

Evidence of differences among study groups was found in HbA1c throughout the study ($p<0.0001$, Table 9), with Composition A ($p<0.0001$) and Composition B ($p<0.0001$) having lower HbA1c than the vehicle, and all the other drug combinations ($p<0.001$). The estimated overall level of HbA1c in the Composition A group (4.75) estimated to be 1.1% absolutely lower than Composition B (5.83, $p<0.0001$). The HbA1c level over the time-course of the study varied between treatments (FIG. 2, interaction: $p<0.0001$). The HbA1c in the Composition A group stayed approximately the same as at baseline. HbA1c increased in Composition B over time but not as much as the other treatments.

Insulin measurements were significantly different among treatments ($p<0.0001$, Table 10) with Composition A ($p<0.0001$) and Composition B ($p=0.0054$) having higher insulin levels at 20 days than the vehicle, and no evidence of a difference between the vehicle and 1K-MET ($p=0.2955$). The Composition A group achieved an estimated average of 10,186 (pg/mL) by day 20, which is significantly greater ($p<0.0001$) than Composition B (5259 pg/mL).

TABLE 10

Effects of combinations of glucose lowering medications on Insulin (pg/mL)

| Comparison | Level | Estimate (95% CI) | P-value |
|---|---|---|---|
| Overall difference between treatments | | | <.0001 |
| Overall level in WBG after dosing (95% CI) | Vehicle | 2947 (1822-4072) | |
| | Composition A | 10186 (9062-11310) | |
| | Composition B | 5259 (4138-6380) | |
| | 1K-MET | 3879 (2757-5001) | |
| Pairwise comparisons | Vehicle vs Composition A | 7239 (5644-8834) | <.0001 |
| | Vehicle vs Composition B | 2312 (723-3901) | 0.0053 |
| | Vehicle vs 1K-MET | 932 (−660-2524) | 0.2445 |
| | Composition A vs 1K-MET | −6307 (−7892−−4722) | <.0001 |
| | Composition B vs Composition A | 4927 (3341-6514) | <.0001 |
| | Composition B vs 1K-MET | −1380 (−2965-206) | 0.0865 |

Figure 3:
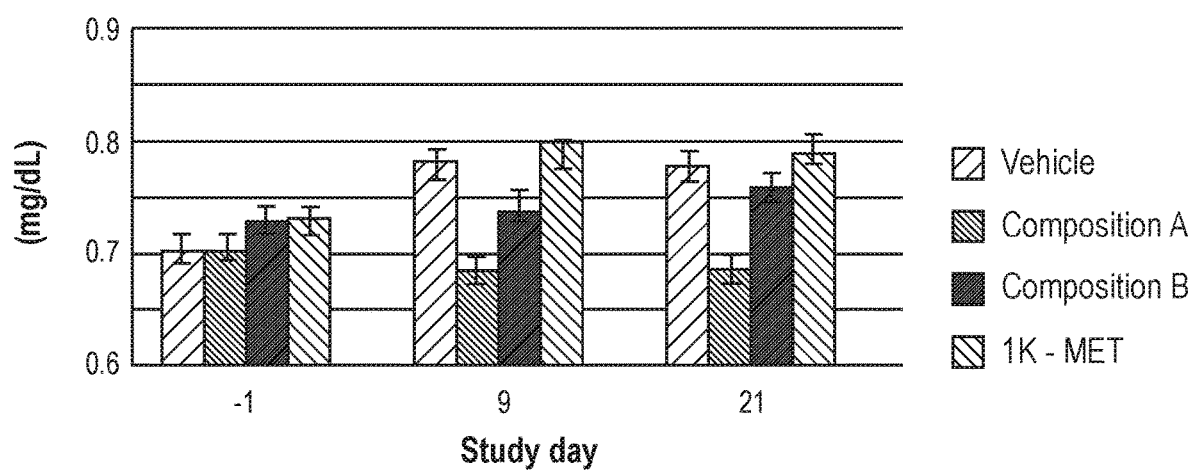
FIG. 3 shows serum Creatinine (mg/dL) post-dosing by treatment group. Error bars represent standard error of the mean (SEM).
Figure 4:
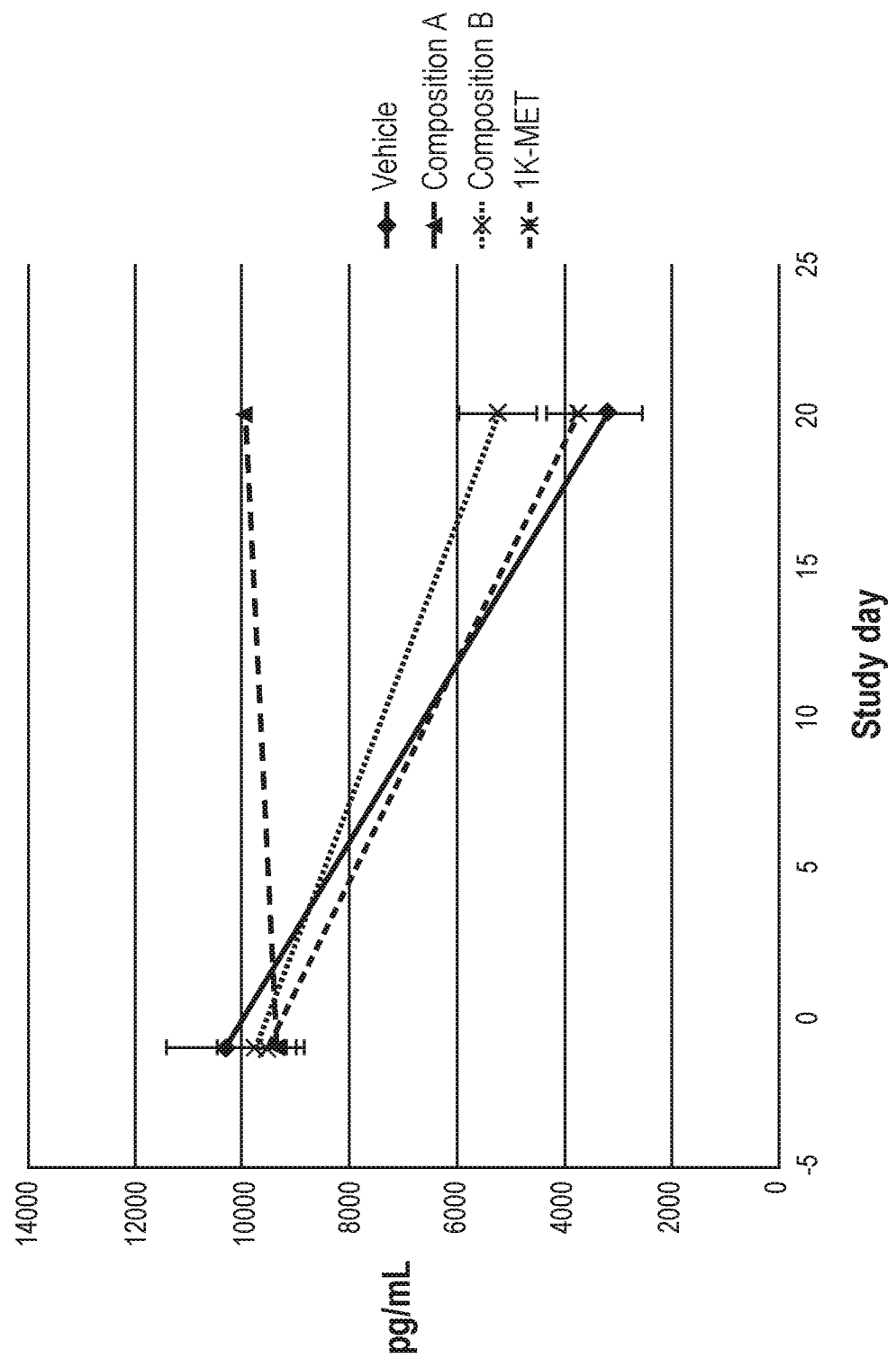
FIG. 4 shows plasma insulin (pg/mL) post-dosing by treatment group.

There was significant ($p<0.0001$) difference in average Creatinine levels between treatment groups. Creatinine levels in the Composition A ($p<0.0001$) and Composition B ($p=0.0082$) groups were lower than the vehicle group. The Composition A group had a significantly lower ($p<0.001$) level of creatinine (0.69 mg/dL) than the Composition B group (0.75 mg/dL). Creatinine levels were similar throughout the study in the Composition A and Composition B groups, with levels increasing in the other study groups (FIG. 3).

TABLE 11

Effects of combinations of glucose lowering medications on Creatinine (mg/dL)

| Comparison | Level | Estimate (95% CI) | P-value |
|---|---|---|---|
| Overall difference between treatments | | | <.0001 |
| Overall level in WBG after dosing (95% CI) | Vehicle | 0.78 (0.76-0.79) | |
| | Composition A | 0.69 (0.68-0.70) | |
| | Composition B | 0.75 (0.74-0.76) | |
| | 1K-MET | 0.79 (0.77-0.80) | |
| Pairwise comparisons | Vehicle vs Composition A | −0.09 (−0.10--0.07) | <.0001 |
| | Vehicle vs Composition B | −0.03 (−0.04--0.01) | 0.0082 |
| | Vehicle vs 1K-MET | 0.01 (−0.01-0.03) | 0.2565 |
| | Composition A vs 1K-MET | 0.10 (0.08-0.12) | <.0001 |
| | Composition B vs Composition A | −0.06 (−0.08--0.04) | <.0001 |
| | Composition B vs 1K-MET | 0.04 (0.02-0.06) | 0.0003 |

TABLE 16

Estimates of outcome by treatment with bootstrap medians and confidence intervals

| Measure | Vehicle | Composition A | Composition B | 1K-MET |
|---|---|---|---|---|
| Whole blood glucose (mg/dL) | 418.6 (399.8-439.4) | 213.3 (186.7-238.5) | 372.5 (334.7-400.8) | 443.4 (419.8-465.0) |
| HbA1c (%) | 6.86 (6.60-7.11) | 4.75 (4.56-4.95) | 5.85 (5.50-6.12) | 6.53 (6.24-6.82) |
| Insulin (pg/m) | 2920 (2119-3828) | 10176 (8675-11747) | 5240 (4084-6531) | 3867 (2914-4874) |
| Creatinine (mg/dL) | 0.78 (0.76-0.79) | 0.69 (0.67-0.70) | 0.75 (0.74-0.76) | 0.79 (0.77-0.80) |

Both of the Composition A and Composition B groups showed lower WBC, HbA1c, reatinine, and higher insulin levels relative to the control group. The 1K-MET group, on the other hand, showed essentially no difference for all the measurements compared to the control.

ULD Compositions A and B reduced blood glucose and HbA1c suggesting a potential therapeutic effect at ultra-low doses. ULD Compositions A and B prevented or reduced the fall in insulin suggesting preserved pancreatic beta-cell function at ultra-low doses. Similarly, ULD Compositions A and B prevented or reduced the increase in creatinine suggesting preserved renal function at ultra-low doses. The effects of triple ULD combinations that included an SGLT-2 antagonist were greater than those of a ULD combination that did not include an SGLT-2 antagonist, suggesting drug-specific treatment benefits. The effects of triple ULD combinations that included an SGLT-2 antagonist were greater than those of standard-dose metformin. The effects of Composition A on all outcomes were greater than Composition B, indicating differences in the effects of ULD dapagliflozin compared with ULD empagliflozin While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating diabetes in a subject in need thereof, comprising administering to the subject a pharmaceutical composition consisting of:
   (a) sitagliptin, or a pharmaceutically acceptable salt or hydrate thereof;
   (b) metformin, or a pharmaceutically acceptable salt or hydrate thereof;
   (c) dapagliflozin or a pharmaceutically acceptable salt or hydrate thereof; and
   (d) at least one pharmaceutically-acceptable excipient;
   wherein a dose of sitagliptin is from about 16.25 mg to about 18.75 mg, a dose of metformin is from about 325 mg to about 375 mg, and a dose of dapagliflozin is from about 2.25 mg to about 2.75 mg,
   wherein the pharmaceutical composition is administered as a single daily dose.

2. The method of claim 1, wherein the subject has persisting elevation of blood sugar after treatment with one or two of (a), (b), or (c) at a lowest diabetes therapeutic dose (LDTD) or higher dose.

3. The method of claim 2, wherein the administration of the pharmaceutical composition is an initial or first-line treatment of diabetes.

4. The method of claim 1, wherein the dose of sitagliptin is about 17.5 mg and the dose of metformin is about 350 mg.

5. The method of claim 1, wherein the dose of sitagliptin is about 17.5 mg and the dose of dapagliflozin is about 2.5 mg.

6. The method of claim 1, wherein the dose of metformin is about 350 mg and the dose of dapagliflozin is about 2.5 mg.

7. The method of claim 1, wherein the pharmaceutically acceptable hydrate of dapagliflozin is dapagliflozin hydrate.

8. The method pharmaceutical composition of claim 7, wherein the pharmaceutically acceptable hydrate of dapagliflozin is dapagliflozin propanediol monohydrate.

9. The method of claim 1, wherein the pharmaceutically acceptable salt of metformin is metformin hydrochloride.

10. The method of claim 1, wherein the pharmaceutically acceptable salt of sitagliptin is sitagliptin phosphate.

11. The method of claim 1, wherein the dose of sitagliptin is about 17.5 mg, the dose of metformin is about 350 mg, and the dose of dapagliflozin is about 2.5 mg.

12. The method of claim 1, wherein the pharmaceutical composition is suitable for oral administration.

13. The method of claim 1, wherein the pharmaceutical composition is in a form of pill, tablet, or capsule.

14. The method of claim 1, wherein the metformin is formulated for immediate release.

15. The method of claim 1, wherein the metformin is formulated for slow release.

\* \* \* \* \*